(12) United States Patent
Stevenson et al.

(10) Patent No.: US 7,113,387 B2
(45) Date of Patent: *Sep. 26, 2006

(54) EMI FILTER CAPACITORS DESIGNED FOR DIRECT BODY FLUID EXPOSURE

(75) Inventors: Robert A. Stevenson, Canyon Country, CA (US); Richard L. Brendel, Carson City, NV (US); John Roberts, Carson City, NV (US); Christine Frysz, Columbia, MD (US)

(73) Assignee: Greatbatch-Sierra, Inc., Carson City, NV (US)

( * ) Notice: Subject to any disclaimer, the term of this patent is extended or adjusted under 35 U.S.C. 154(b) by 22 days.

This patent is subject to a terminal disclaimer.

(21) Appl. No.: 11/136,843

(22) Filed: May 24, 2005

(65) Prior Publication Data

US 2005/0219787 A1 Oct. 6, 2005

Related U.S. Application Data

(63) Continuation of application No. 10/778,954, filed on Feb. 12, 2004, now Pat. No. 6,985,347, which is a continuation-in-part of application No. 10/377,086, filed on Feb. 27, 2003, now Pat. No. 6,765,779.

(60) Provisional application No. 60/360,642, filed on Feb. 28, 2002.

(51) Int. Cl.
*H01G 4/35* (2006.01)
*H01G 4/236* (2006.01)
*H01G 4/228* (2006.01)

(52) U.S. Cl. .................. 361/302; 361/307; 361/306.2; 607/5

(58) Field of Classification Search ................ 361/302, 361/306.1, 306.2, 306.3, 307, 308.1, 308.2, 361/308.3, 309–311, 301.2; 607/5; 333/182–185
See application file for complete search history.

(56) References Cited

U.S. PATENT DOCUMENTS

| | | | |
|---|---|---|---|
| 2,756,375 | A | 7/1956 | Peck |
| 3,235,939 | A | 2/1966 | Rodriguez et al. |
| 3,538,464 | A | 11/1970 | Walsh |
| 3,920,888 | A | 11/1975 | Barr |
| 4,083,022 | A | 4/1978 | Nijman |
| 4,144,509 | A | 3/1979 | Boutros |
| 4,148,003 | A | 4/1979 | Colburn et al. |
| 4,152,540 | A | 5/1979 | Duncan et al. |
| 4,220,813 | A | 9/1980 | Kyle |
| 4,247,881 | A | 1/1981 | Coleman |
| 4,314,213 | A | 2/1982 | Wakino |

(Continued)

*Primary Examiner*—Eric W. Thomas
(74) *Attorney, Agent, or Firm*—Kelly Lowry & Kelley, LLP

(57) ABSTRACT

An EMI filter capacitor assembly utilizes biocompatible and non-migratable materials to adapt electronic components for direct body fluid exposure. The assembly includes a capacitor having first and second sets of electrode plates which are constructed of non-migratable biocompatible material. A conductive hermetic terminal of non-migratable and biocompatible material adjacent to the capacitor is conductively coupled to the second set of electrode plates. One or more conductive terminal pins having at least an outer surface of non-migratable and biocompatible material are conductively coupled to the first set of electrode plates, while extending through the hermetic terminal in non-conductive relation. The terminal pins may be in direct contact with the first set of electrode plates, or in contact with a termination surface of conductive connection material. The termination surface is also constructed of non-migratable and biocompatible materials. Layers of glass may be disposed over surfaces of the assembly, including the capacitor.

38 Claims, 17 Drawing Sheets

U.S. PATENT DOCUMENTS

| | | |
|---|---|---|
| 4,352,951 A | 10/1982 | Kyle |
| 4,362,792 A | 12/1982 | Bowsky et al. |
| 4,424,551 A | 1/1984 | Stevenson |
| 4,456,786 A | 6/1984 | Kyle |
| 4,737,601 A | 4/1988 | Gartzke |
| 4,741,710 A | 5/1988 | Hogan et al. |
| 5,032,692 A | 7/1991 | DeVolder |
| 5,070,605 A | 12/1991 | Daglow et al. |
| 5,142,430 A | 8/1992 | Anthony |
| 5,333,095 A | 7/1994 | Stevenson et al. |
| 5,440,447 A | 8/1995 | Shipman et al. |
| 5,539,611 A | 7/1996 | Hegner et al. |
| 5,670,063 A | 9/1997 | Hegner et al. |
| 5,751,539 A | 5/1998 | Stevenson et al. |
| 5,825,608 A | 10/1998 | Duva et al. |
| 5,905,627 A | 5/1999 | Brendel et al. |
| 5,959,829 A | 9/1999 | Stevenson |
| 5,973,906 A | 10/1999 | Stevenson |
| 5,978,204 A | 11/1999 | Stevenson |
| 6,008,980 A | 12/1999 | Stevenson |
| 6,055,455 A | 4/2000 | O'Phelen et al. |
| 6,349,025 B1 * | 2/2002 | Fraley et al. ............... 361/302 |
| 6,414,835 B1 * | 7/2002 | Wolf et al. ................. 361/302 |
| 6,437,970 B1 * | 8/2002 | Lee et al. ................... 361/311 |
| 6,790,881 B1 * | 9/2004 | Date et al. .................. 523/205 |

* cited by examiner

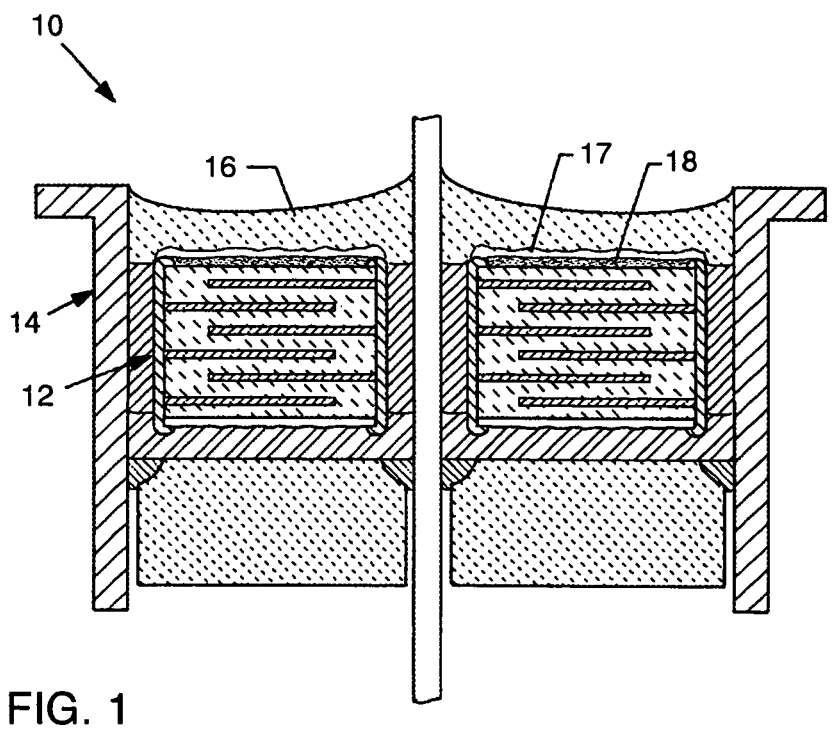
FIG. 1
PRIOR ART
FIG. 2
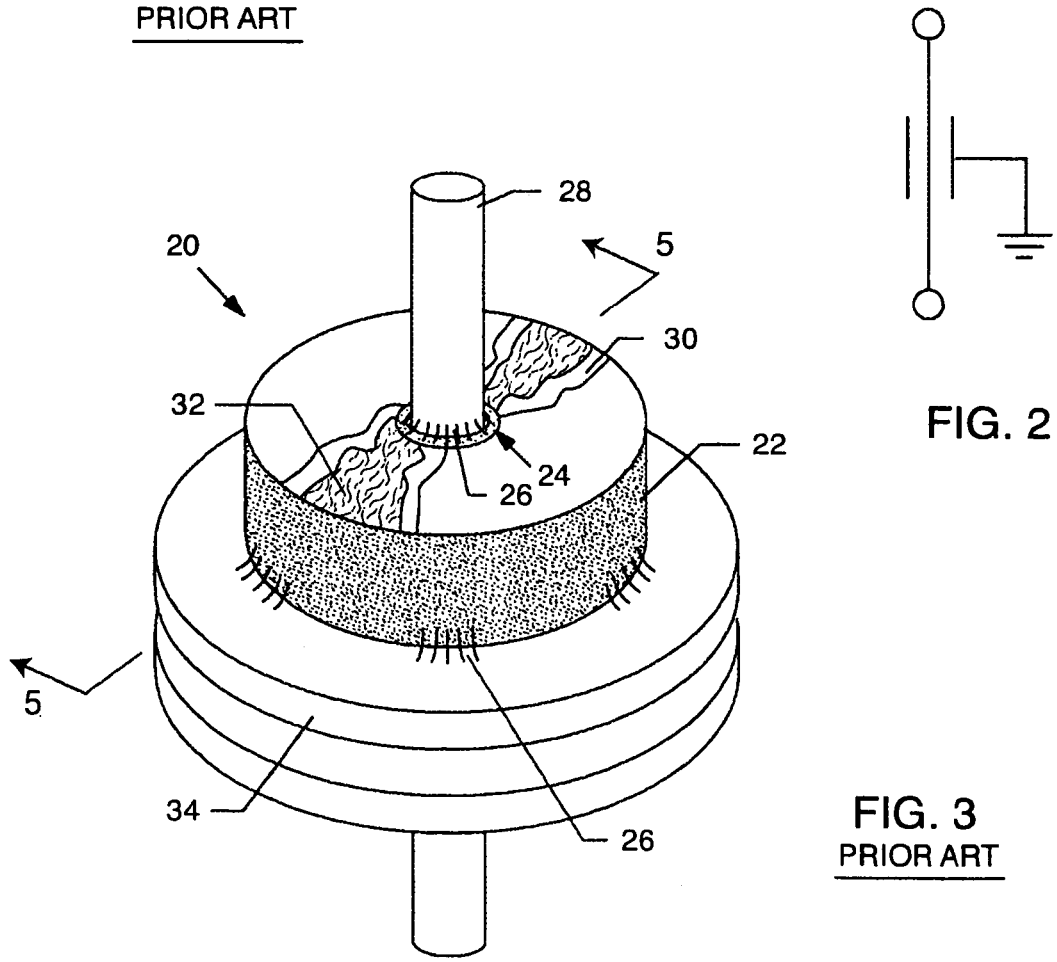
FIG. 3
PRIOR ART

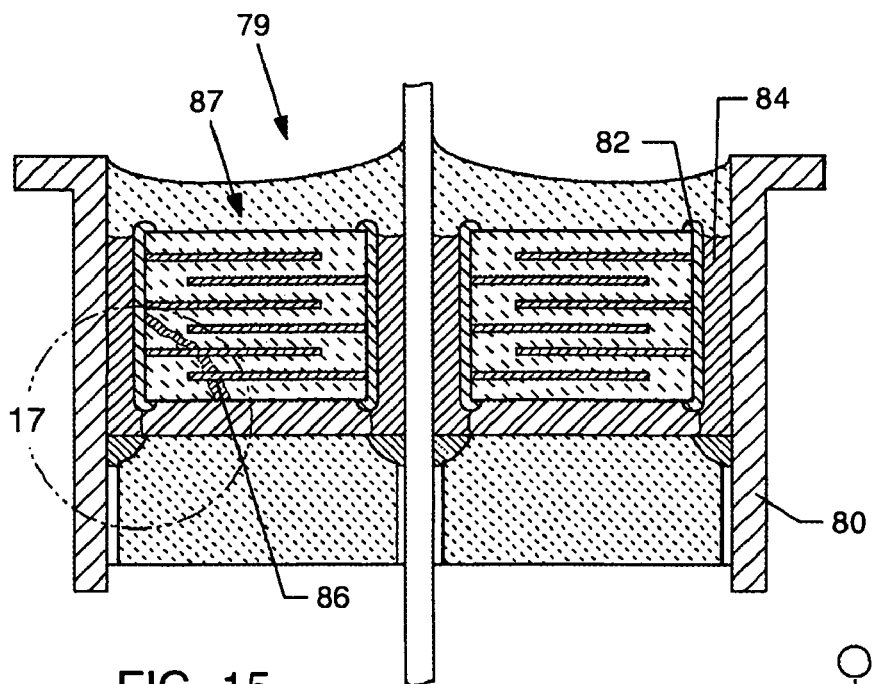
FIG. 15
PRIOR ART
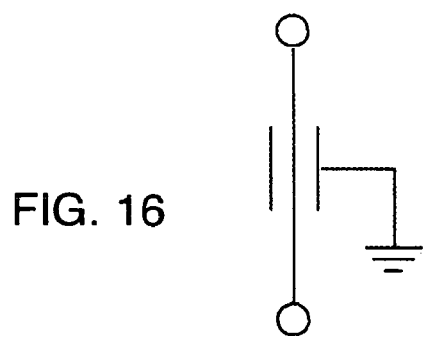
FIG. 16
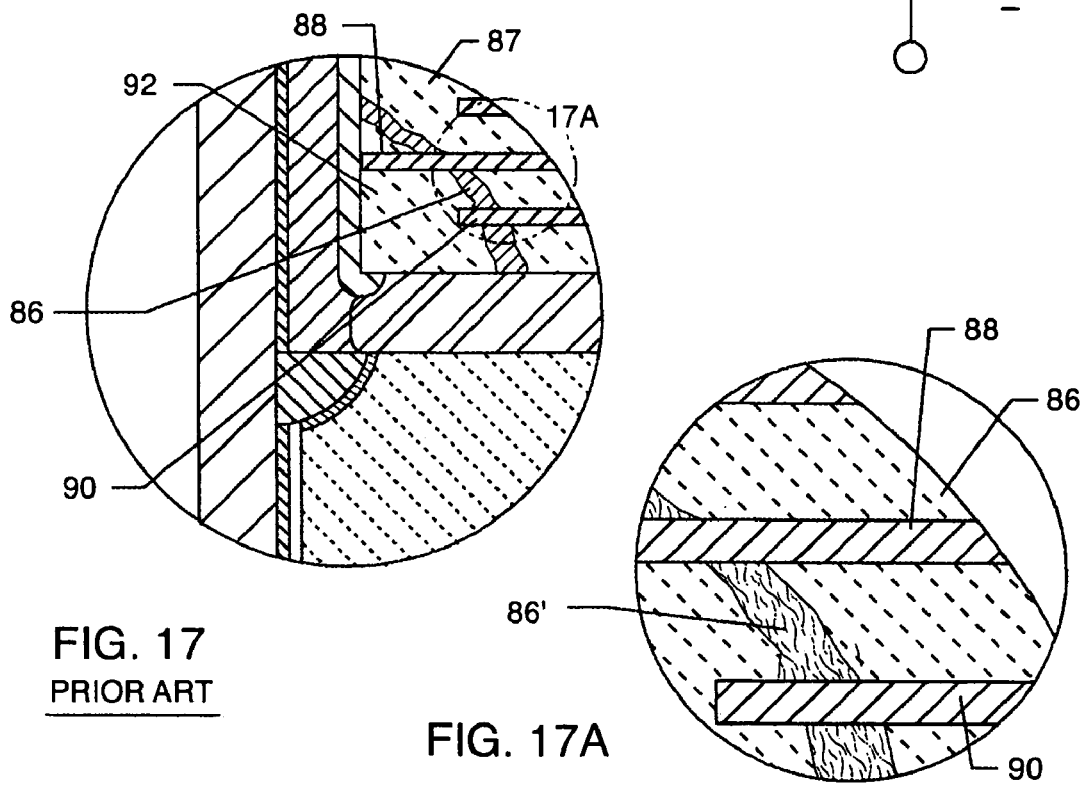
FIG. 17
PRIOR ART
FIG. 17A

EMI FILTER CAPACITORS DESIGNED FOR DIRECT BODY FLUID EXPOSURE

RELATED APPLICATION

This application is a continuation of U.S. Ser. No. 10/778,954, filed Feb. 12, 2004 (now U.S. Pat. No. 6,985,347), which is a continuation-in-part of U.S. Pat. No. Application Ser. No. 10/377,086, filed Feb. 27, 2003 (now U.S. Pat. No. 6,765,779), which claims benefit from U.S. Provisional Patent Application Ser. No. 60/360,642, filed Feb. 28, 2002.

BACKGROUND OF THE INVENTION

This invention relates generally to feedthrough capacitor terminal pin subassemblies and related methods of construction, particularly of the type used in implantable medical devices such as cardiac pacemakers (bradycardia devices), cardioverter defibrillators (tachycardia), neuro-stimulators, internal drug pumps, cochlear implants, ventricular assist devices, and other medical implant applications, to decouple and shield undesirable electromagnetic interference (EMI signals) signals from the device. More specifically, this invention relates to materials and methods of manufacturing monolithic ceramic feedthrough capacitors so that they can be exposed to body fluid.

It is well known in the art that EMI feedthrough capacitors can be attached to the flanges of human implantable hermetic seals for reliable EMI filter performance. These EMI filters are very important to bypass and attenuate RF signals from undesirable emitters, such as cell phones, microwave ovens and the like.

These devices are generally designed with one or more monolithic ceramic feedthrough capacitors or monolithic ceramic rectangular chip capacitors designed to be in intimate relation with the hermetic terminal. In general, monolithic ceramic capacitors are considered to be sensitive electronic components and are not manufactured of biocompatible materials. Monolithic ceramic capacitors are typically constructed of a barium titinate dielectric into which active and ground electrode plates are interspersed. It is common in the art that the ceramic capacitor dielectric be of barium titinate, zirconium titinate, or other high dielectric constant ceramic materials with various dopants added to control its dielectric constant, temperature stability and electrical properties. Barium titinate in itself is biocompatible; however, the electrodes and the termination materials are generally not biocompatible. Typical monolithic ceramic capacitors would include a palladium-silver, or nickel silver electrode system (base metal electrode). Other electrode systems are possible, including ternary, which is a high fire system consisting of an alloy of gold, platinum and palladium.

Typical capacitor termination materials are applied in two ways. The first system involves a glass frit, which is loaded with metallic particles along with a binder and vehicle system to make a paste. This paste is then applied to the capacitor and fired into place. The conductive particles make contact to the exposed electrode plates and place them in parallel. A properly formed capacitor termination is a highly conductive surface to which one can make electrical connections through soldering or other methods. Typical materials used for this glass frit are a silver or copper loaded glass frit or a palladium silver or platinum silver composition. Silver is relatively inexpensive and highly conductive and is also available in a wide variety of flakes and spherical shapes. Accordingly, it is well known in the art to build a monolithic ceramic capacitor using such termination material.

The second methodology involves plating of the termination. There are a number of plating methods currently used in the art, including a barrier plating technique which consists of plating down nickel and then various materials on top of the nickel to promote solderability. The nickel acts as a barrier layer and prevents leaching off of the capacitor. For example, if tin or copper were plated on top of the nickel, the tin or copper would readily wet with solder and the nickel would form a layer resistant to leaching or removal from the capacitor. Therefore, in nearly all of the prior art devices the monolithic ceramic capacitor is placed on the inside of the implantable medical device. In other words, this places the sensitive monolithic ceramic capacitor away from the body fluid so that it cannot come in contact with the body fluid. Another way of stating this is that a hermetic terminal is used to prevent intrusion of body fluid into the interior of the electronic device. Accordingly, all of the electronic circuits, including the substrate, circuit boards, battery, computer chips, capacitors and electromagnetic interference capacitors, are placed in a suitable location inside the titanium housing of the implantable medical device so that they are protected from body fluids.

However, modern pacemakers and implantable defibrillators tend to be very small in size and very cramped in terms of space inside the unit. Thus, placing the capacitor on the outside of the housing increases the volumetric efficiency of the overall design, such as by allowing a larger battery to be inserted in the device housing. In addition, laser welds used to seal the housing, typically comprised of titanium, will have a lesser effect on the capacitor.

Recognizing this, U.S. Pat. No. 6,055,455 discloses a monolithic ceramic capacitor placed on the outside (or the body fluid side) of the hermetic terminal of an implantable medical device. In this patent the concept of decoupling the EMI before it gets to the inside of the pacemaker or the implantable medical device is emphasized. However, it makes no difference from a filter effectiveness point of view whether the capacitor is on the inside surface or on the outside surface of the hermetic seal.

Electromagnetic interference consists of a number of modulated carrier frequencies, for example, the carrier frequency of a typical cellular phone. What is important is that the gap between the feedthrough capacitor and the hermetic seal be a wave-guide beyond cut off. In other words, that gap needs to be small enough so that the wavelength of the electromagnetic interference will not readily pass through it. As it turns out, after doing wave-guide calculations, this is relatively easy to do for a medical implant application. One reason for this is the human body's tendency to reflect and absorb EMI at frequencies of 3 GHz and above. In other words, it really makes no difference whether the EMI feedthrough capacitor is on the body fluid side or the inside of the hermetic terminal of an implantable medical device. The closely spaced feedthrough capacitor presents such a small wave-guide that it would take frequencies in excess of 20 GHz to effectively re-radiate around the filter. However, as previously mentioned, at frequencies of 3 GHz and above the human body is so effective in attenuating such signals that higher frequencies are really not of importance.

A significant mistake found in the prior art is the notion that adding some sort of an adjunct sealant over the top of a monolithic ceramic feedthrough capacitor will allow it to operate in the presence of body fluids. Body fluid is an extremely corrosive and conductive medium. There are many dissolved minerals in body fluid, including salt and potassium, which readily conduct electricity in their ionic state. Polymers and adjunct sealants and conformal coatings on electronic components have a number of weaknesses which include problems with adhesion and also bulk permeability. Simply stated, over a long period of time moisture can still penetrate through any adjunct non-hermetic sealant and eventually reach the capacitor. In addition, adjunct sealants and coatings have a different thermal coefficient of expansion as compared to the barium titinate ceramic capacitor. Thus, after exposure to temperature excursions or simply after a long period of time, the adhesion of the coating to the capacitor surface starts to break down. This could allow a thin film of moisture or body fluid to be present at the surface of the ceramic capacitor. In fact, any slight separation of any of the adjunct sealant could cause a small gap or tightly spaced separation into which moisture could easily form. One way that moisture can form in such a tiny space is through dew point condensation. That is, during temperature excursions moisture laden or vapor laden air could enter such a small separation and then deposit out as a thin film of moisture.

One of the most common and severe failures of electronic components comes from a process known as metal migration, whisker formation or dendritic growth. A dendrite can form of various migratable materials, including silver, tin, and the like. Another common way of describing this phenomenon is through tin or silver whiskers. Once these dendrites form across the surface of the capacitor, the capacitor's insulation resistance drops dramatically. This can short out the capacitor, thereby shorting out the entire implantable medical device. The effect could also be degraded insulation resistance, which could result in reduced battery life or in reduced functionality of the output waveform of the implantable medical device.

FIG. 1 is a cross-sectional view of a prior art unipolar capacitor 10, similar to that described by U.S. Pat. No. 4,424,551, the contents of which are incorporated herein. At first glance it would appear that the capacitor 12, shown inside the ferrule 14, is well protected against body fluid by the sealant 16, such as an epoxy seal. However, in actual practice there is a mismatch of thermal coefficient of expansion between the polymers and the barium titinate of the ceramic capacitors. There are also adhesion problems and difficulties with bulk permeability. Accordingly, across both the top and bottom surfaces of the capacitor 12 one can usually see, at high magnification, a small separation 17 is often present between the sealing material and the capacitor surface itself. This would be a separation on the top surface of the capacitor 12 and sealing material 16 due to a separation in the bond between non-conductive sealing material 16 and the capacitor 12. After a prolonged period of time, moisture can penetrate into either one of these spaces. Accordingly, a metal migration or dendrite 18 can form either on the top or bottom of the capacitor 12. As mentioned above, the formation of this dendrite could lead to either immediate or latent catastrophic failure of the implanted medical device.

With reference to FIGS. 3–5, a prior art unipolar feedthrough capacitor 20 mountable to a hermetic terminal of an implantable medical device, such as a cardiac pacemaker, an implantable cardioverter defibrillator (ICD) a cohlear implant, or the like is shown. Such prior art capacitors 20 are typically constructed using a silver-bearing or palladium silver bearing-glass frit for the outside diameter termination surface 22 as well as the inner diameter surface 24. Connecting material 26 connects the capacitor's lead wire 28 to the inside diameter surface 24 of the feedthrough capacitor 20. The material 26 is typically of a silver-filled conductive polyimide, or a lead or tin bearing solder or the like. If the capacitor 20 were exposed and placed on the body fluid side of the medical device, a thin film of moisture 30 would be present across the surface of the capacitor. This moisture could be present from direct immersion in body fluid or from the penetration of any adjunct sealants by body fluids. In the presence of moisture 30, dendrites or metal migration 32 would form or grow between the areas of opposite polarity 22 and 24. This dendritic growth or migration can also occur from the capacitor's outside diameter metallization material and the material used to make the electrical mechanical connection between the capacitor lead wire 28, and the capacitor's inside diameter 24. Even if the capacitor's outside diameter termination material 22 was of biocompatible material, (which is not typical in the prior art), the connection material 26 which forms the electromechanical connection from the capacitor outside diameter 22 to a ferrule 34, could still be problematic. That is due to the fact that the connecting material 26 is typically a silver-filled conductive thermosetting polymer, such as a conductive polyimide or the like.

Thus, in the presence of moisture and a voltage bias, the silver is free to migrate and form dendrites 32 as shown in FIGS. 3 and 5. Of course those skilled in the art will realize that the formation of these dendrites 32 is highly undesirable because they are conductive and tend to lower the insulation resistance or short out the capacitor 20. This is particularly problematic in a low voltage pacemaker application. In cardiac pacemaker applications, the formation of the silver, tin or other dendrites 32 would preclude the proper operation of the implanted medical device. Another undesirable effect of the formation of these dendrites 32 is that they would tend to conduct current and thereby dissipate power unnecessarily, leading to premature battery failure of the implanted medical device. Premature battery failure is highly undesirable and leads to unwanted surgery and increased expense, usually the replacement of the entire implantable medical device.

With reference now to FIGS. 6 and 7, a surface mounted quadpolar capacitor 36 is illustrated, such as that described in U.S. Pat. No. 5,333,095, the contents of which are incorporated herein. As can be seen from the illustration, dendrites 38 or 38' can form between any points of opposite polarity as long as there is migratable material as well as a migratable medium. As previously mentioned, migratable mediums include thin films of moisture, solvents or the like. Accordingly, another problem can arise during cleaning or washing of the capacitor 36. Any entrapped cleaning solvents, such as alcohol, water or degreasers along with a bias voltage can allow for the migration of the metallic migratable materials. It will be appreciated by those skilled in the art that not only can the dendrites 38 form between lead wires of opposite polarity 40, but also at 38' between two lead wires of the same polarity and an adjacent ground at the capacitor outside diameter metallization 42. Both conditions are highly undesirable in that the dendrite 38 formation could short out or reduce the insulation resistance between the two lead wires thereby degrading any biological signal sensing that they may perform. The term "short out" does not necessarily imply that the dendrite 38 will form a zero ohm connection because the resistance of the dendrite, metal migration or whisker depends upon a number of factors including the thickness density and length of the dendrite 38 or 38' that is formed. Dendrites do not form a continuous sheet, but rather are discontinuous. Time lapse photography has shown that dendrites form side branches similar to a tree with many leaves. Accordingly, what results is a matrix of silver conductive particles that have many strange geometric shapes. Accordingly, the resistivity of such a structure is highly variable, ranging from several thousand ohms down to a very few ohms.

With reference to FIG. 8, an in-line quadpolar capacitor 44 is illustrated wherein the outside or ground termination 46 is in two localized areas. Such localization minimizes the opportunity for dendrites to form. However, when the electrical connection is made between the termination material 46 and the conductive ferrule material 48 using a connective material 50 which is comprised of migratable material, typically a silver-filled solder or conductive thermal-setting polymer such as a conductive polyimide or the like, the formation of dendrites 52 or 52' is possible in the presence of moisture. A dendrite 52 could form between the capacitor conductive metallization 46 and lead wire 54 or a dendrite 52' could form between lead wires 54, as illustrated.

With reference to all of the illustrated prior art, when the capacitor is installed in the housing of an implantable medical device and the capacitor is oriented toward the inside, such dendrites typically do not form. This is because the inside of the implantable device is hermetically sealed. This prevents intrusion of body fluids or other moisture. In addition, the active implantable medical device is typically thoroughly cleaned and then baked dry prior to assembly. The device is then laser welded shut. Prior to final sealing, the interior of the implantable medical device is evacuated at high vacuum and then back-filled with dry nitrogen. In other words, the ceramic capacitors of the prior art are never really exposed to moisture throughout their design life. Accordingly, the dendrites 52 in FIG. 8 do not have a chance to form when the capacitor is oriented to the inside of a properly constructed active implantable medical device.

FIG. 10 illustrates a prior art internally grounded bipolar feedthrough filter capacitor 56, such as that disclosed in U.S. Pat. No. 5,905,627 the contents of which are incorporated herein by reference. Even though the capacitor 56 has no outside diameter or outside perimeter metallization, a dendrite 58' can still form if a moisture film and voltage bias form between the lead wires 60 and 66 or a dendrite 58 can form between a lead wire 60' and a conductive ferrule 62. In this case, the conductive ferrule 62 has been greatly simplified and shown as a rectangular plate. In the art, these ferrules 62 take on a variety of sizes and shapes, including H-flanges to capture the mating halves of an implantable medical device housing. As shown, the dendrite 58 has formed all the way from the conductive material to the ferrule 62 used to make the connection between the capacitor lead wire 60 and the capacitor inside diameter 64, which would typically be a conductive polyimide solder or the like. In an internally grounded feedthrough capacitor 56, there is always a grounded lead wire 66 which is connected to the capacitor's internal electrode plate set 68, illustrated in FIG. 12. It is also possible, or even likely, to form a dendrite 58' between this lead wire and any adjacent lead of opposite polarity. Such a dendrite 58' would short out the lead wire 60 to the grounded lead wire 66. This is why coating such leads, which may be formed of noble metal material, with migratable metals or materials such as tin-lead combinations, is problematic. Thus, it will be readily apparent by those skilled in the art that dendrites can form and migrate over any migratable conductive material, such as silver-filled conductive thermal-setting connective material which is often used to connect lead wires 60 and 66 to the inside diameter metallization 64 of the feedthrough capacitor or conductively connect the outside of the capacitor to the ferrule 62.

It should be noted that for a dendrite to form, the migratable material need not be present on both sides. In other words, a migratable material is not necessarily both the cathode and the anode. There are no materials in titanium that would migrate, however, silver particles from conductive silver bearing glass frit fired onto the capacitor is capable of migrating in the presence of a voltage bias and a moisture film. It is also possible that a dendrite material form directly between the inside diameter metallizations 64 from the ground feedthrough hole and one or more of the active insulated feedthrough capacitor wires.

Detecting the presence of these dendrites can sometimes be very confusing for the test technician. This is because the dendrites most readily form in a high-impendence, low voltage circuit where a moisture film is present along with migratable materials. The dendrite, metal migration or metal whisker is typically very lacy, thin and of low cross-sectional area. Accordingly, this material can act like a fuse and open up if a high voltage or a low impedance voltage or current source is applied. Accordingly, when dendrites are present, they are sometimes inadvertently blown open by routine electrical testing either by the manufacturer or by the customer's receiving inspection department. A concern is that after years of field use, if the dendrite were to reform, this could slowly degrade the battery life of the medical device through decreased insulation resistance or degrade the device's ability to sense very low level biological signals. These are yet again reasons why it has been common in the prior art to always place the ceramic feedthrough capacitor toward the inside where it is protected from body fluids.

FIG. 13 shows a prior art integrated chip capacitor 70, such as that described in U.S. Pat. Nos. 5,959,829 and 5,973,906, the contents of which are incorporated herein. These chip capacitors 70 come in a variety of sizes and shapes and are used to decouple electromagnetic interference from the lead wires 72 of an implantable medical device to the metallic ferrule 74. As illustrated, capacitor 70 has integrated four rectangular chip style capacitors into a single monolithic package. Each of these chip capacitors makes a connection to the lead wire 72 and decouples EMI to the metallic ferrule 74. Since prior art chip capacitors are constructed of the same materials as are typical in the entire capacitor industry, it is likely that a dendrite 76 will form if moisture or solvents are present. Such dendrites 76 can form between the migratable connective materials used to connect the capacitor metallization 78 to the lead wire 72 and the ferrule 74, or between the lead wires 72 (not shown).

It is a common misconception that it takes many months or years for metal migration or dendrites to form. Actually, the dendrite itself has been observed to form very quickly so long as a migratable material, a moisture or solvent film, and a suitable bias voltage is present. Once these three factors come together, it can be only a matter of seconds or minutes for the dendrite itself to actually form. As previously mentioned, dendrites can also form from lead wires to the conductive materials used to connect the capacitor's ground termination to the conductive ferrule. This is the case even if the ferrule is of a non-migratable material such as titanium or a noble metal, such as gold or the like, provided that the connective material is of a migratable material such as silver, tin, or other known migratable metals. As can been seen, there are many ways for such dendrites to form. Notwithstanding U.S. Pat. No. 6,055,455, the inventors are not aware of a single instance in an implantable medical device where the capacitor has been placed on the outside and exposed to body fluid. Instead, it has been standard practice in the medical implant industry that all electronic components be protected inside the hermetically sealed enclosure, which is typically vacuum evacuated and back filled with an inert gas such as nitrogen or the like to ensure a very dry atmosphere, and prohibit contact with body fluids. Of course, in such a dry atmosphere, one of the three essential ingredients for metal migration or dendrite formation is removed and such dendrites do not form.

Metal migration, whiskers and dendrite formation does not only occur of the surfaces of ceramic feedthrough and chip capacitors. Said dendrites can also form inside the capacitor along microfractures, cracks, or knit line defects (slight separations in the capacitor electrode lamination boundary). Internal metal migration within a ceramic capacitor can have the same catastrophic effects as surface migration. That is, the insulation resistance of the capacitor can be severely reduced including the shorting out of the capacitor completely.

The ceramic feedthrough capacitor which acts as an EMI filter is poised directly at the point of ingress and egress of the lead wires between the implantable medical device and body tissue. For example, in a cardiac pacemaker, the feedthrough capacitor is placed at the point where lead wires from the heart enter into the pacemaker itself. Accordingly, any short circuiting or lowering of insulation resistance of the ceramic feedthrough capacitor precludes or shorts out the proper operation of the pacemaker itself. This can be very dangerous or even life threatening to a pacemaker-dependent patient whose heart depends on each pulse from a pacemaker so that it itself will beat. There are numerous instances in the literature wherein cardiac pacemakers, implantable defibrillators and neurostimulators have been shown to adversely react in the presence of an emitter such as a cell phone or retail store security gate (electronic article surveillance system). Pacemaker potential responses to EMI include sensing (pacemaker inhibition), noise reversion to asynchronous spacing, tracking for dual chamber devices, in rate adaptive devices the rate changes within programmed rate limits, activation of the lead switch, ICD undersensing, asynchronous pacing, or microprocessor reset. In an implantable cardioverter defibrillator (ICD), potential responses to EMI can include all of the responses for a pacemaker in that ICDs often include a pacemaker function. In addition, ICDs may also respond to EMI by over-sensing that manifests itself as either inhibition or an inappropriate delivery of therapy. An inappropriate delivery of therapy means that a fully alert and cognizant patient would receive a high voltage shock. Delivery of such a high voltage can injure the patient by literally throwing him off his feet (such a case has been documented with the male patient breaking his arm). In addition, ICDs can respond to EMI by tracking, undersending an arrhythmia, or electrical current directly induced in the lead system that can trigger a dangerous cardiac arrhythmia. Accordingly, proper operation of the EMI filter is critical to protect the implantable medical device from not exhibiting any of the possible aforementioned malfunctions. Formation of dendrites can seriously degrade the proper operation of the pacemaker and/or make the filter ineffective at performing its proper function.

For example, with reference to FIGS. 15–17, a cross-sectional view of a prior art unipolar feedthrough capacitor assembly 79 is shown similar to that described in U.S. Pat. Nos. 4,424,551; 4,152,540; 4,352,951 and others. Monolithic ceramic capacitors have a relatively low thermal coefficient of expansion compared to metals. Ceramic capacitors are very strong in compression, but very weak in tension. This is typical of most brittle materials. Accordingly, it is very easy to introduce cracks within the ceramic capacitor structure if the capacitor is subjected to excessive stresses. The ceramic capacitor assembly shown in FIG. 15 has the ceramic capacitor embedded within a metallic ferrule 80. For a human implant application, this metallic ferrule 80 would typically be made of titanium and could have a variety of shapes and flanges. The connection from the inside diameter of the ferrule 80 to the outside diameter metallization 82 of the feedthrough capacitor is shown as material 84. Material 84 is typically a thermal-setting conductive adhesive, such as a silver-filled conductive polyimide, epoxy or the like. The entire assembly shown in FIG. 15 is designed to be installed into a pacemaker, ICD or the like by laser welding directly into the titanium can of the implantable device. Accordingly, the ferrule 80 is rapidly heated and tends to expand. The relatively cooler ceramic capacitor 79 does not expand nearly at the same rate. Accordingly, a variety of cracks can be introduced into the ceramic capacitor. These cracks can be axial, radial or cover sheet type features.

For purposes of example, as shown in FIG. 17, a crack 86 has propagated across the corner of the ceramic capacitor 87. Additionally, the crack 86 has contacted plates 88 and 90 of opposite polarity. In other words, the crack 86 has propagated through the main body of the ceramic dielectric 92 between a ground electrode plate 88 and the lower active electrode plate 90. This in and of itself does not present an immediate electrical defect. The reason for this is that as long as the crack 86 itself does not contain metallic particles, the two electrodes 88 and 90 are not shorted out. However, it is quite possible for these cracks to propagate to the outside diameter or top surface of the capacitor 87. Long-term exposure to body fluid in combination with the bulk permeability of the surrounding polymers can lead to the presence of a moisture thin film that lines the inside of this crack 86. FIG. 17A shows a silver dendrite 86' that has formed by metal migration through the cracks. The reason for the formation of the dendrite has to do with the intrinsic materials that are typically used in the prior art electrodes and capacitor terminations themselves. Ceramic capacitors are typically made with nickel, silver or palladium silver electrodes. These are low cost electrode systems that are found in many ceramic capacitors today. They are formed within the solid monolithic ceramic by firing or sintering at a relatively low temperature (around 1100° C.). As previously mentioned, an internal dendrite is a highly undesirable situation to occur because this shorts out the ceramic capacitor. Such shorting or reduced insulation resistance of the ceramic capacitor not only degrades its effectiveness as an EMI filter, it also can cause the catastrophic failure of the entire implantable medical device. As mentioned, this can be life threatening, for example, in the case of a pacemaker-dependant patient. The dendrite can be low enough in resistance to short out the pacemaker output pulse. In this case, the patient's heart would simply stop beating, which would quickly lead to death.

Accordingly, there is a need for a feedthrough filter capacitor which can be disposed on the body fluid side of an implantable device to provide additional space for an enlarged battery, a smaller implantable device, etc., while being immune to dendritic growth. The present invention fulfills these needs and provides other related advantages.

SUMMARY OF THE INVENTION

As noted above, three ingredients are needed for such catastrophic or latent metal migration defects to occur: 1) the presence of a migratable material, which may include silver, tin, and many other materials; 2) a migratable medium, such as a thin film of moisture or solvent; and 3) an activation energy such as an applied voltage. On the outside of a cardiac pacemaker which is implanted in body fluid and has a small output voltage, two of these three elements are always present. That is, the migratable medium and the activation energy. Activation energy is present in most active implantable medical devices, including cardiac pacemakers, implantable cardioverter defibrillators, neuro-stimulators, cochlear implants, and the like.

For a feedthrough capacitor mounted on the body fluid side, another challenge is the inner connection between the ceramic feedthrough capacitor or chip capacitor and the lead wires and also the ferrule or the hermetic terminal. In an electromagnetic interference attenuation application, it is important that the capacitor active electrodes be connected to each lead wire and its ground electrodes connected to the ground. As defined herein, ground is the potential of the overall electromagnetic shield, which in the case of a pacemaker is usually titanium, but may be of a titanium alloy, stainless steel, tantalum, ceramics, niobium, or the equivalent. The ferrule is typically laser welded to this overall titanium can or housing. Therefore the titanium can or housing forms an equipotential surface to which EMI can be bypassed by the feedthrough or chip capacitor.

The use of solders to make the electrical connection between the capacitor and its lead wires or the capacitor and the ferrule, is generally ruled out. The reason for this is that most solders contain either lead or tin, both of which are not biocompatible. The problems with lead are obvious from all of the literature regarding lead poisoning in the human body. Tin is ruled out because it is not biocompatible plus it will readily form whiskers or dendrites. Even exotic gold alloy solders still usually contain a percentage of tin or lead, which rules them out for similar reasons. The trouble with other conducting materials such as a conductive polyimide or conductive epoxy is that the polymer is loaded with a silver powder, such as a silver flake or a silver sphere, which is not tightly bound up chemically and is free to migrate. This is also true of the prior art ceramic capacitor metallization materials. For example, a silver bearing glass frit which is fired onto the capacitor will readily form a dendrite. Accordingly, it is a novel feature of the present invention that the third ingredient, namely, migratable materials exposed to the migratable medium, be removed. Thus, a preferred embodiment of the present invention resides in an EMI filter capacitor assembly adapted for direct body fluid exposure by being constructed of biocompatible and non-migratable materials, particularly in locations where body fluid exposure occurs. Alternatively, or in addition, the filter capacitor includes a protective barrier, preferably glass, which prevents the body fluid from contacting such conductive and critical portions of the capacitor assembly.

Thus, in general, the EMI filter capacitor assembly which is adapted for direct body fluid exposure comprises a capacitor having first and second sets of electrode plates which comprise a non-migratable and biocompatible material. A conductive hermetic terminal comprises a non-migratable and biocompatible material and is adjacent to the capacitor so as to be in conductive relationship to the second set of electrode plates. A conductive terminal pin, having an outer surface comprising a non-migratable and biocompatible material at least where exposed to body fluid, is in conductive relationship with the first set of electrode plates and extends through the hermetic terminal in non-conductive relation.

The first and second sets of electrode plates and the outer surface of the terminal pin are typically comprised of a noble metal or a noble metal composition. For example, these structures may be comprised of gold, tantalum, niobium, platinum, a gold-based alloy or a platinum-based alloy. The hermetic terminal, usually in the form of a ferrule, comprises a material selected from titanium, a titanium alloy, stainless steel, tantalum, a tantalum alloy, niobium, a niobium alloy, gold, a gold alloy, platinum, and a platinum alloy. Such biocompatible and non-migratable materials avoid the harmful formation of dendrites, as explained above.

Other biocompatible metals and alloys that can be used for the ferrule, capacitor metallization, capacitor electrode, or capacitor connection materials include all of the metals and alloys of titanium, platinum and platinum iridium alloys, tantalum, niobium, zirconium, Hafnium, nitinol, Co—Cr—Ni alloys such as MP35N, Havar®, Elgiloy®, stainless steel and gold. There are also a number of conductive metal compounds that can be used including ZrC, ZrN, TiN, NbO, TiC, and TaC.

In several embodiments of the present invention, the capacitor includes a first termination surface comprising a non-migratable and biocompatible material that conductively couples the first set of electrodes and is in conductive relation to the terminal pin. The capacitor also includes a second termination surface, which also comprises a non-migratable and biocompatible material, that conductively couples the second set of electrodes and is in conductive relation to the hermetic terminal.

Usually, a connection material is used to connect the terminal pin to the first termination surface, and the hermetic terminal to the second termination surface. The conductive connection materials are typically thermal-setting, brazing, welding or soldering materials. So as to be non-migratable, these materials are selected from the group consisting of: gold, gold alloy, platinum, gold-filled-thermal-setting conductive material, platinum-filled-thermal-setting conductive material, gold-bearing glass frit, TiCuSil, CuSil, and gold-based braze.

Table 1 below shows a more comprehensive list of polymers that can also be filled with any of the biocompatible metals mentioned above. This list can include a variety of epoxies and polyimide materials in addition to polyethylene oxide with ionic additions such as NaCl or any of the other commonly used implantable polymers including polyurethane, silicone, polyesters, polycarbonate, polyethylene, polyvinyl chloride, polypropylene, methylacrylate, paraxylylene and polypyrrhol. As mentioned, any of these can be made conductive with a biocompatible material, for example, by adding a particulate filler such as platinum or gold powder. There are other materials that could be used including pyrolytic carbon and Tra-Duct 2902 conductive adhesive.

An insulator is usually disposed between the capacitor and the ferrule, and a hermetic seal connects the insulator and the ferrule. The hermetic seal is comprised of a non-migratable material, at least where exposed to the body fluid, and is typically selected from the group consisting of: gold, gold alloy, platinum, glass, TiCuSil, CuSil, and other gold-base compounds.

In one embodiment of the present invention, the capacitor is a monolithic structure which includes an electrode portion as well as an insulator portion.

The capacitor may be chip capacitor or a feedthrough capacitor. In the instance of a feedthrough capacitor, the one or more terminal pins will extend through one or more passageways of the capacitor.

In one feedthrough capacitor embodiment of the present invention, the conductive terminal pin is in direct physical contact with the inner first termination surface of the capacitor. In alternative embodiments, there is no first termination surface and instead the one or more terminal pins are in direct physical contact with the active first electrode set. To facilitate this, a portion of the terminal pin may have an irregular surface, such as a knurled surface. Similarly, the second termination surface may be omitted with the second set of ground electrodes either by directly contacting the hermetic terminal, or conductively coupled thereto with a biocompatible conductive material, as described above.

In another embodiment, the filter capacitor assembly includes a capacitor having a glass layer disposed on a top surface thereof. A glass layer may also be disposed on a bottom surface thereof. This glass layer adds strength to the capacitor, but is also intended to prevent body fluid contact with the first and second termination surfaces as well as conductive connectors of the capacitor assembly to prevent dendrites from forming. As added protection, the capacitor assembly may be comprised of the non-migratable materials, as described above, as well as having glass layers disposed thereon.

Other features and advantages of the present invention will become apparent from the following more detailed description, taken in conjunction with the accompanying drawings, which illustrate, by way of example, the principles of the invention.

BRIEF DESCRIPTION OF THE DRAWINGS

The accompanying drawings illustrate the invention. In such drawings:

FIG. 1 is a cross-sectional view of a prior art unipolar capacitor having an adhesive seal on a top surface thereof, illustrating a small separation formed between a sealing material and a top surface of the capacitor where dendrites may form;

FIG. 2 is an electrical schematic diagram of the capacitor of FIG. 1;

FIG. 3 is a perspective view of a prior art unipolar feedthrough capacitor mounted to a hermetic terminal of an implantable medical device, and having dendritic growth thereon;

FIG. 15 is a cross-sectional view of a prior art unipolar capacitor, having cracks and dendritic growth between electrodes thereof;

FIG. 16 is an electrical schematic diagram of the capacitor of FIG. 15;

FIG. 17 is an enlarged view of area 17 of FIG. 15, illustrating the crack and dendritic growth between electrodes;

FIG. 17A is an enlarged view of area 17A of FIG. 17, illustrating dendritic growth within the crack;

DETAILED DESCRIPTION OF THE PREFERRED EMBODIMENTS

As shown in the accompanying drawings for purposes of illustration, the present invention resides in EMI filter assemblies which are adapted for direct body fluid exposure without the formation of harmful metal migration, dendritic growth, or whiskers.

Figure 5:
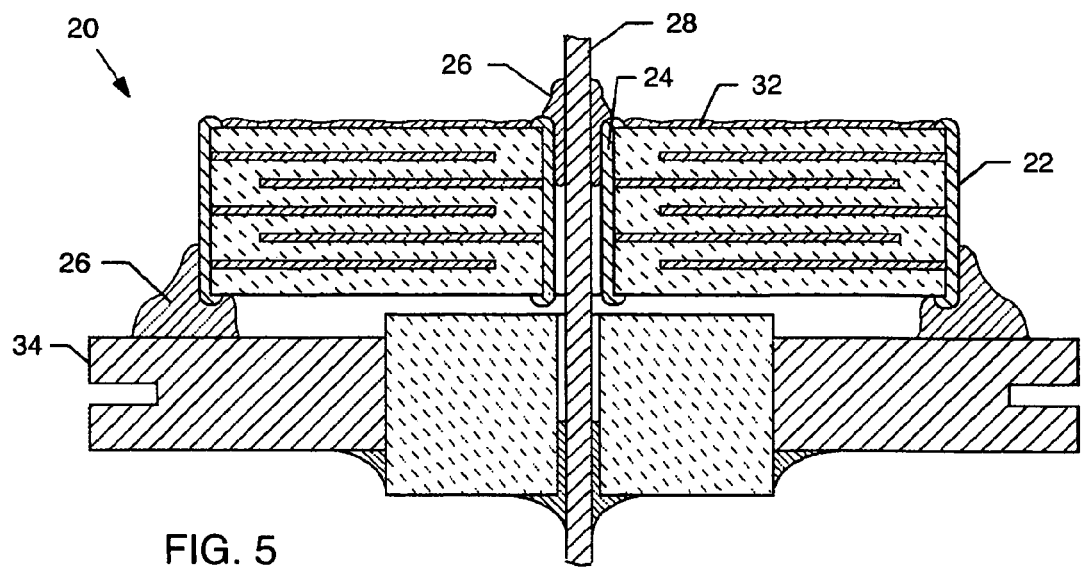
FIG. 5 is a cross-sectional view taken generally along line 5—5 of FIG. 3, illustrating internal components of the capacitor assembly.
Figure 6:
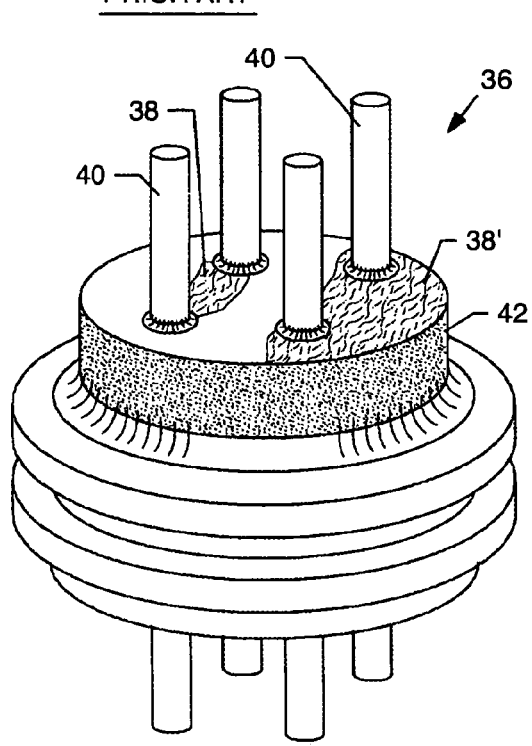
FIG. 6 is a perspective view of a prior art surface mounted quadpolar capacitor, illustrating dendritic growth between lead wires and/or lead wires and ground thereof.
Figure 4:
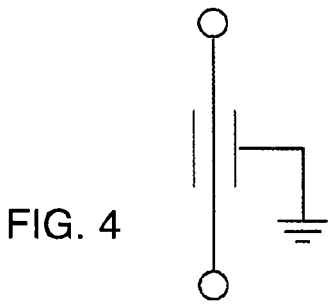
FIG. 4 is an electrical schematic diagram of the capacitor of FIG. 3.
Figure 7:
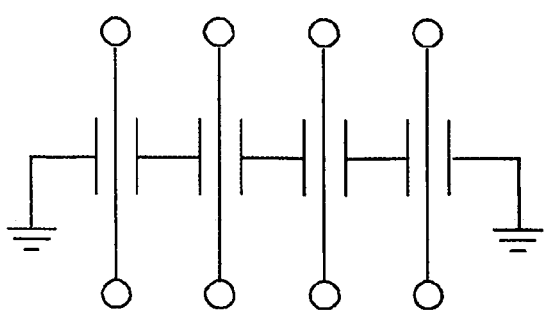
FIG. 7 is an electrical schematic diagram of the capacitor of FIG. 6.
Figure 8:
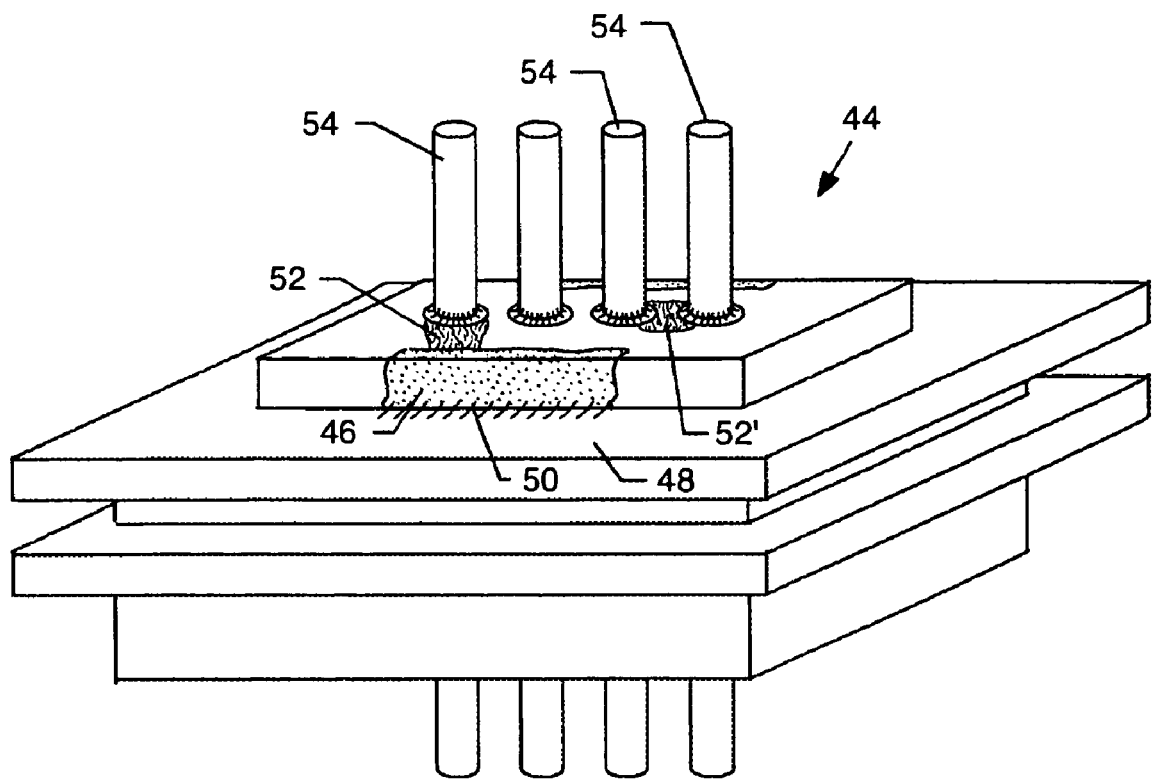
FIG. 8 is a perspective view of a prior art in-line quadpolar capacitor, illustrating dendritic growth between conductive portions thereof.
Figure 9:
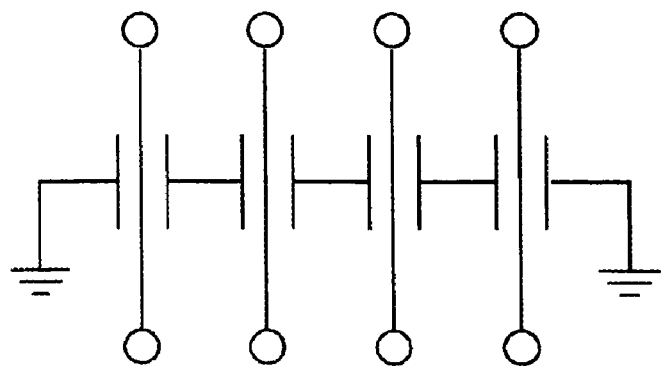
FIG. 9 is an electrical schematic diagram of the capacitor of FIG. 8.
Figure 10:
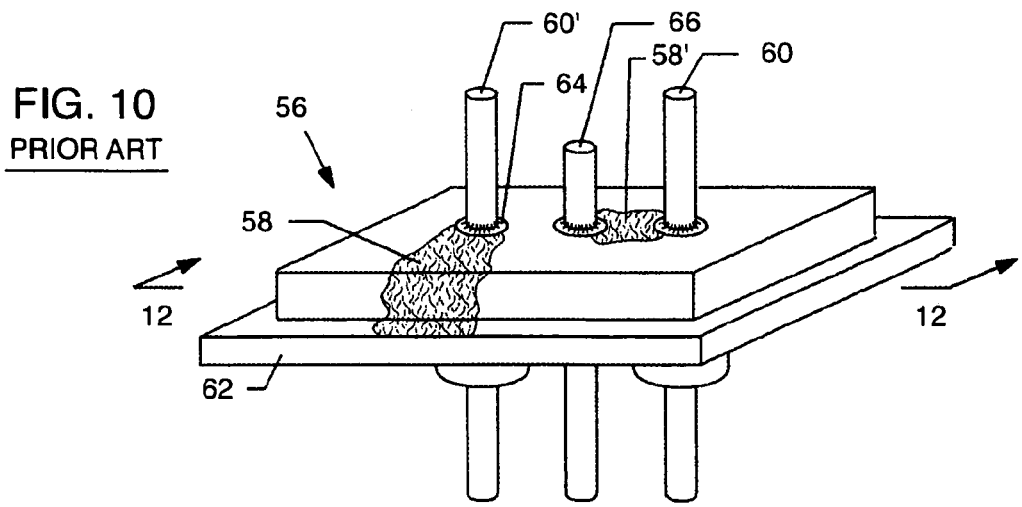
FIG. 10 is a perspective view of a prior art internally grounded bipolar feedthrough capacitor having dendritic growth between conductive portions thereof.
Figure 11:
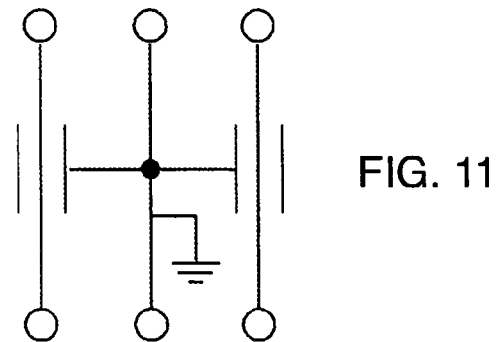
FIG. 11 is an electrical schematic diagram of the capacitor of FIG. 10.
Figure 12:
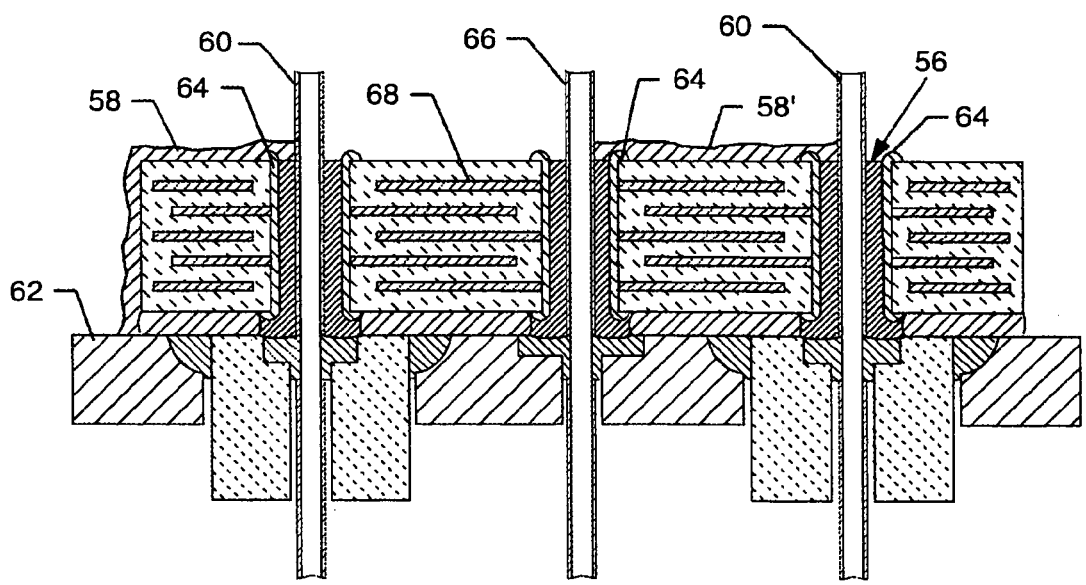
FIG. 12 is a cross-sectional view taken generally along line 12—12 of FIG. 10, illustrating internal components thereof and dendritic growth formed thereon.
Figure 13:
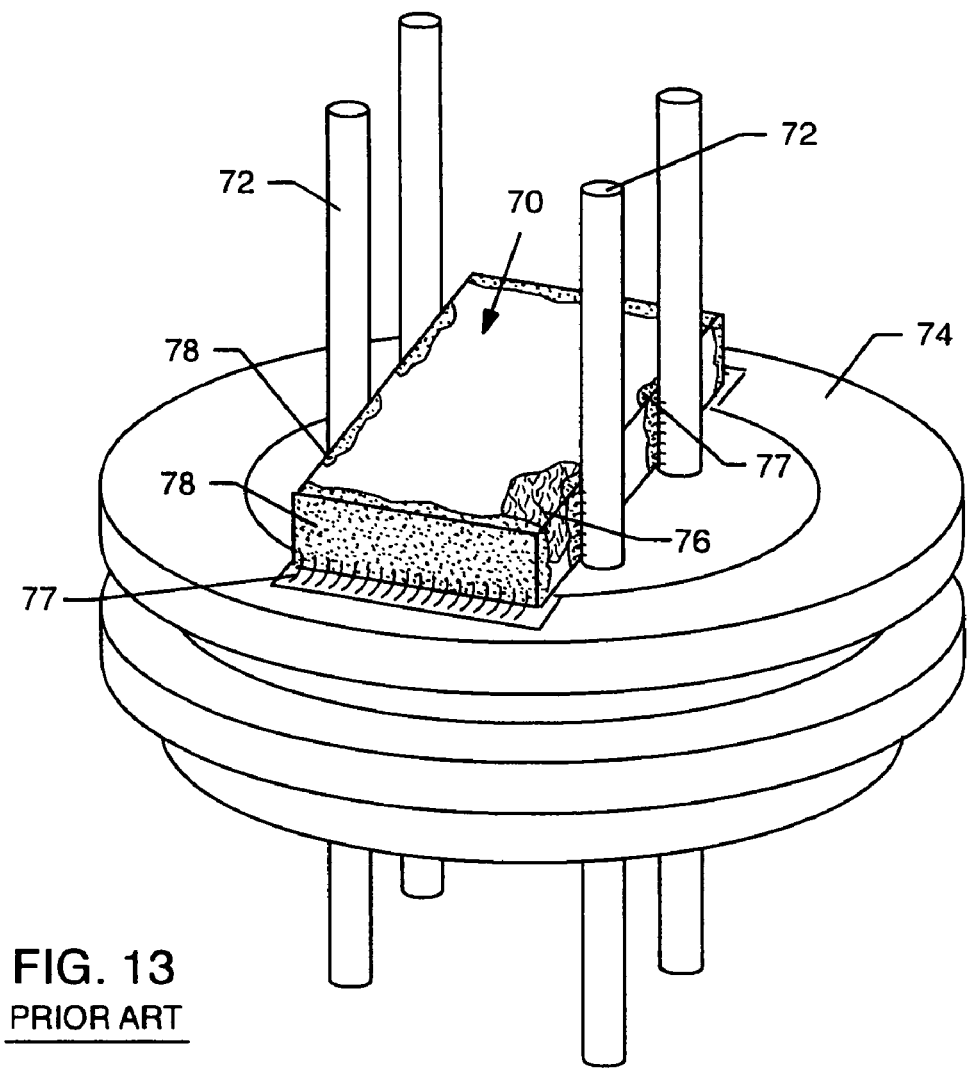
FIG. 13 is a perspective view of a prior art integrated chip capacitor having dendritic growth thereon.
Figure 14:
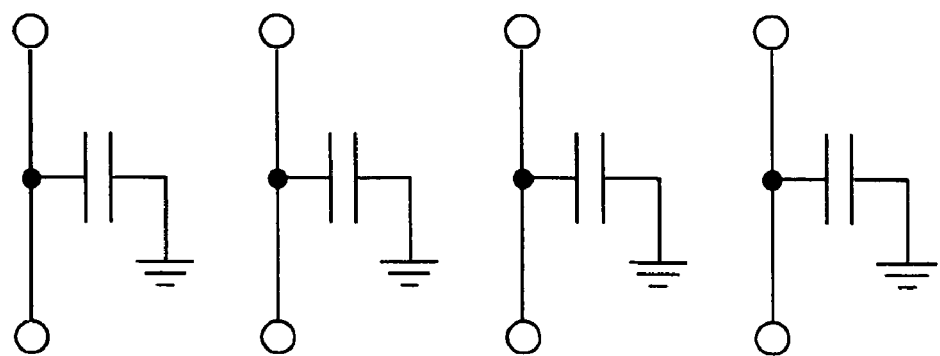
FIG. 14 is an electrical schematic diagram of the chip capacitor of FIG. 13.
Figure 18:
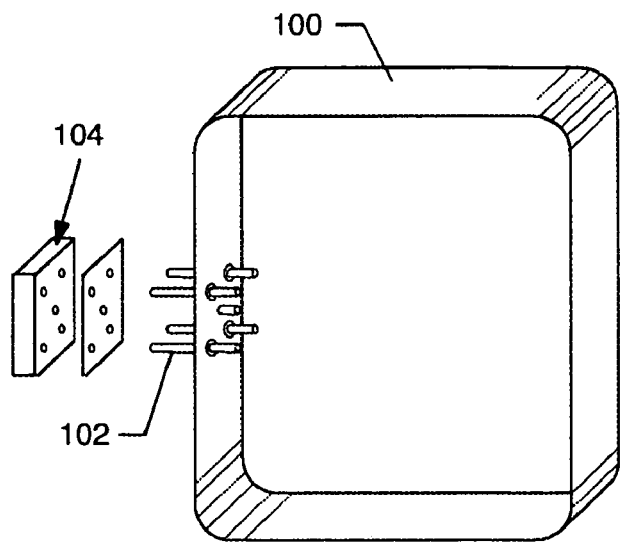
FIG. 18 is a diagrammatic view of an EMI filter assembly disposed on the outside of a hermetically sealed can used in medical devices, in accordance with the present invention.
Figure 19:
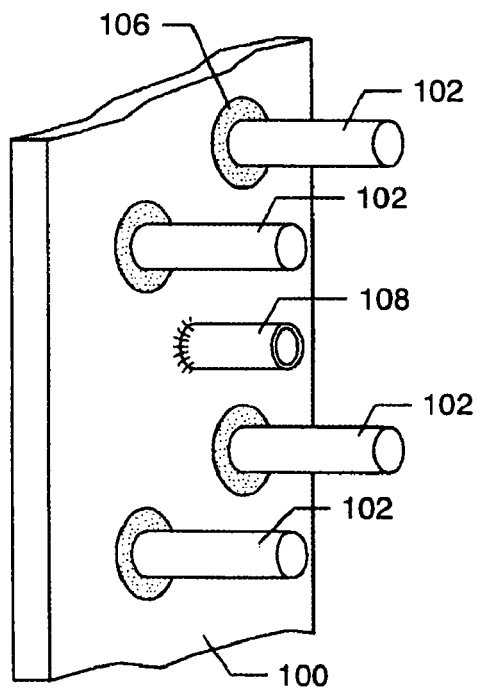
FIG. 19 is a partially fragmented and enlarged perspective view of leads extending from the can of FIG. 18.
Figure 20:
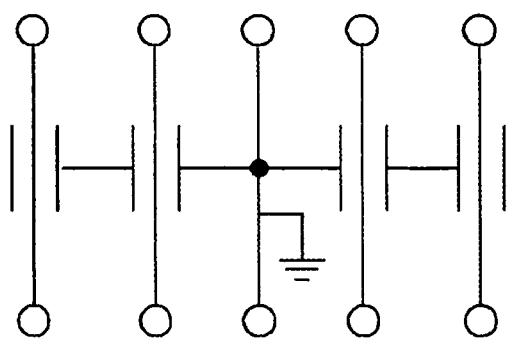
FIG. 20 is an electrical schematic diagram of the assembly of FIG. 18.

With reference to FIGS. 18–20, a metal can or housing 100 is illustrated which is exemplary of those used to enclose the electronics of an implantable medical device, such as a pacemaker or the like. These electronics typically include a battery, a circuit board, integrated circuits, and a variety of other components and sensors (not shown). In the prior art, as described above, the capacitor is disposed within the housing 100, which is closed, such as by welding, and hermetically sealed to protect all of the interior electronic components from the intrusion of body fluids or other contaminants. Terminal pins or lead wires 102 extend into the housing 100 in insulative relationship with the housing and pass through an EMI feedthrough filter capacitor, as is well-known in the art.

However, using the present invention, the capacitor 104 can be disposed outside of the housing 100, advantageously saving space on the inside of the unit housing 100. In order to accomplish this, the feedthrough capacitor 104 and the lead wires 102 are all formed of non-migratable materials, such as noble metals, which do not migrate in the presence of electrical bias and body fluid.

As described above, it takes three ingredients to form a dendrite or to et up the conditions for metal migration. Previously, the ingredient that was removed is the moisture or thin film by inserting the capacitor 104 within the housing 100 which is hermetically sealed. Thus, migratable materials such as in, or silver along with a bias voltage could be present without harm. However, in the presence of body fluid, or other moisture, any migratable material present can and will lead to the formation of metal migration, dendrites and the like. Thus, it is a primary feature of the present invention that the capacitor is designed to operate in the presence of moisture or moisture films by utilizing non-migratable materials, such as noble metals and alloys, that cannot migrate.

In FIG. 19, an enlarged view of the lead wires 102 extending through the housing 100 is shown. Each of the lead wires 102 is in insulative relationship with the housing 100 by insulating material 106, which is shown for illustrative purposes. It will be obvious to one skilled in the art that there are a variety of methodologies that can be used to maintain the four lead wires 102 in non-insulative relationship with the metallic can or housing 100. These include the use of alumina insulators, glass seals, or a ferrule or individual unipolar ferrules with gold-brazed alumina insulators. The center ground pin 108 may be hollow, as illustrated, whereby after hermetic sealing by laser welding of the lid of the housing (not shown) one could then use the hollow ground pin 108 to pull a vacuum and then back fill the inside with dry nitrogen. While still in a nitrogen tank, hollow tube 108 would then be hermetically sealed by welding, ball insertion or the like. The capacitor illustrated in FIG. 18 is of the internally grounded type, which simplifies the assembly. However, it will be appreciated by those skilled in the art that it is not necessary that the capacitor 104 be of internally grounded construction, instead surface mounted technology such as that described by U.S. Pat. No. 5,333,095 or other capacitor types so long as it is constructed of materials in accordance with the present invention so that the capacitor can be disposed in direct contact with body fluids outside of the housing 100 of the medical device.

Figure 21:
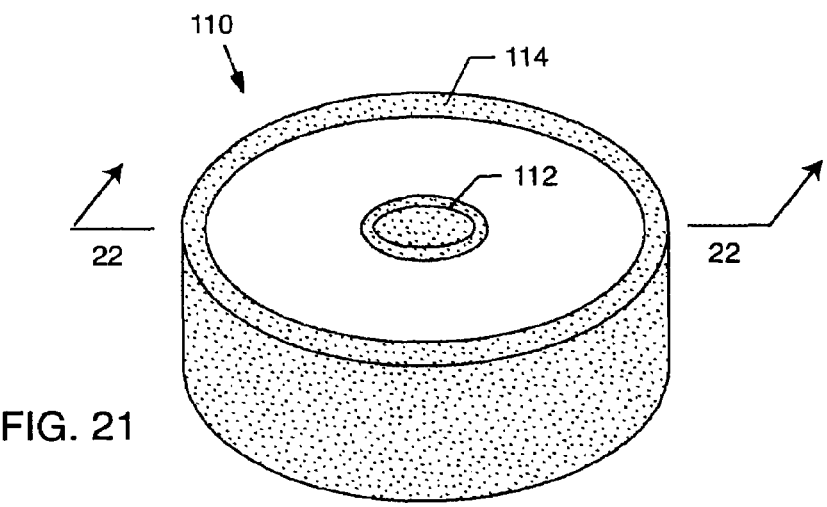
FIG. 21 is a perspective view of a unipolar capacitor comprised of non-migratable materials in accordance with the present invention.

FIG. 21 illustrates a monolithic feedthrough ceramic capacitor 110 having metallization of non-migratable materials on an inner terminal surface 112 and an outer terminal surface 114. The capacitor 110 may be constructed using conventional manufacturing methods, in terms of silkscreen, punching, hole drilling, and the like. However, the metallization materials for the inner and outer termination surfaces 112 and 114 are typically comprised of a noble metal or alloy, such as pure gold, pure platinum, or the like. Other metals include titanium, platinum/iridium alloys, tantalum, niobium, zirconium, hafnium, nitinol, stainless steel and Co—Cr—Ni alloys such as MP35N, Havar® and Elgiloy®. See Table 1 below. These metals are biocompatible and are also known to not migrate or form dendrites in the presence of moisture or body fluid solutions. It should be understood that the termination surfaces 112 and 114 can be coated with the noble metals or alloys which are non-migratable, or comprised entirely of such metals. The important aspect is that those portions that are potentially in contact with moisture be of non-migratable material to prevent dendritic growth.

TABLE 1

LIST OF CONDUCTIVE, ATTACHABLE, NON-MIGRATING BIOCOMPATIBLE MATERIALS

| Metals and Alloys | Conductive Metal Compounds | Polymers* |
|---|---|---|
| Titanium | ZrC | Polyethylene Oxide with ionic addition such as NaCl (see U.S. Pat. No. 6,295,474) |
| Platinum and platinum/iridium allows | ZrN | Polyurethane |
| Tantalum | TiN | Silicone |
| Niobium | NbO | Polyesters |
| Zirconium (often used in knee joint replacements) | TiC | Polycarbonate |
| Hafnium | TaC | Polyethylene |
| Nitinol | | Polyvinyl Chloride |
| Co—Cr—Ni alloys such as MP35N, Havar®, Elgiloy® | | Polypropylene |
| Stainless Steel | | Mathylacrylate |
| Gold (has been used as a stent coating) | | Para-xylylene |
| | | Polypyrrhol |
| | | Epoxies |
| | | Polyimides |

*Any of the commonly used implantable polymers mentioned above can be made conductive by adding a particulate filler such as Pt powder.
Others: Pyrolytic carbon and Tra-Duct 2902 conductive adhesive.

Figure 22:
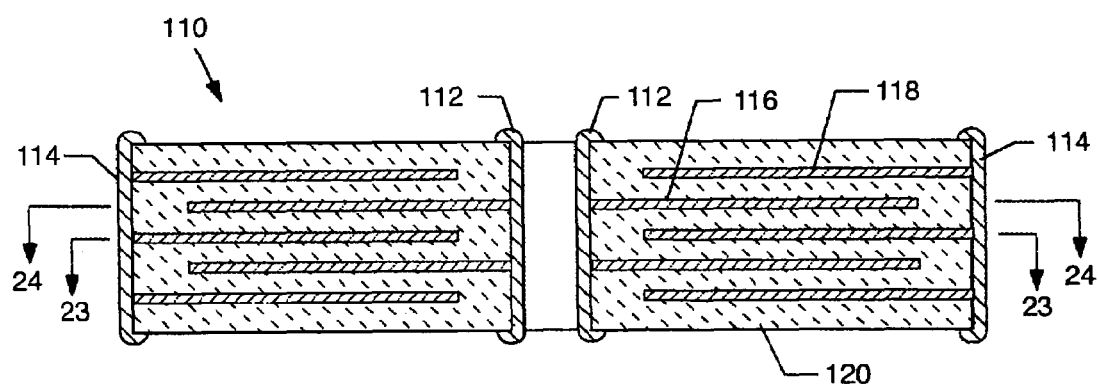
FIG. 22 is a cross-sectional view taken generally along line 22—22 of FIG. 21.
Figure 23:
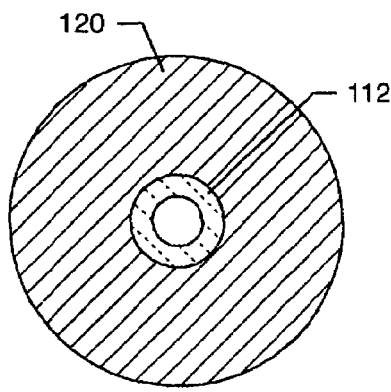
FIG. 23 is a cross-sectional view of the capacitor of FIGS. 21 and 22 along the line 23—23 in FIG. 22, illustrating the layout of conductive ground electrode plates therein.
Figure 24:
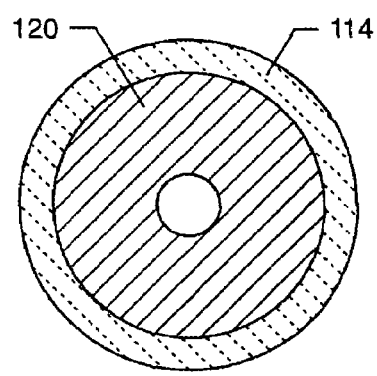
FIG. 24 is a cross-sectional view taken along the line 24—24 in FIG. 22, illustrating the layout of active electrode plates therein.

FIG. 22 is a cross-section of the novel unipolar feedthrough capacitor of FIG. 21.

Within the capacitor 110 are active 116 and ground 118 electrodes. As cracks can form in the non-conductive or dielectric material 120 filling the capacitor 110 and separating the electrodes 116 and 118, thus possibly leading to dendritic growth between the electrodes 116 and 118, in a particularly preferred embodiment of the present invention the electrodes 116 and 118 are also formed of non-migratable material. Preferably, these electrodes 116 and 118 are constructed of platinum or a platinum alloy. The use of platinum electrodes 116 and 118 enables the capacitor to be a high fire capacitor. That is, the capacitor would have to be sintered at a much higher temperature than is typically used in the industry. However, there are other materials which could be used which would form suitable alloys that would not tend to migrate. For example, a ternary system, comprised of an alloy of gold, platinum palladium, could be used. The use of ternary electrodes is known, however, never in combination with the other material described herein and never used in a human implant application where direct body fluid exposure would be expected.

Figure 25:
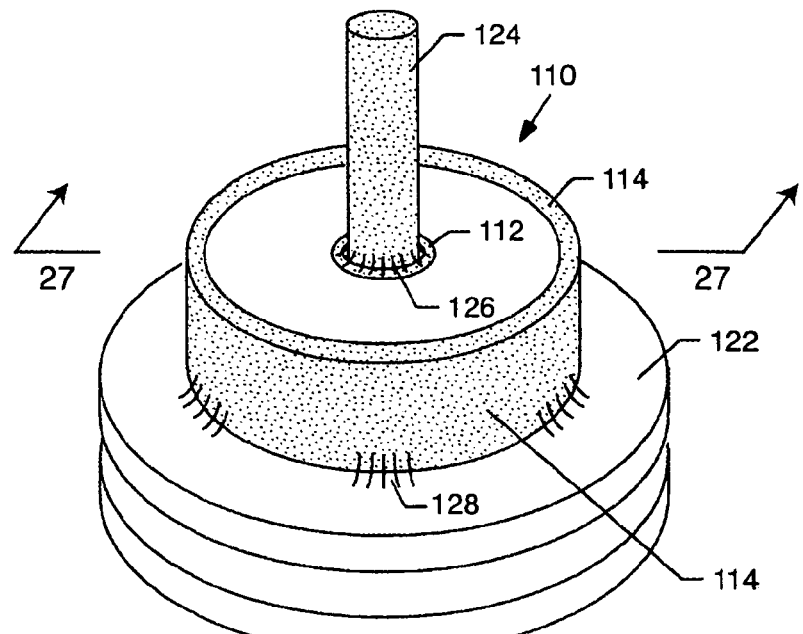
FIG. 25 is an isometric view of the capacitor of FIG. 21, having a lead wire extending therethrough and attached to a hermetic terminal of a human implantable electronic device.
Figure 26:
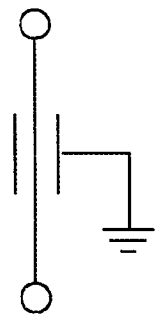
FIG. 26 is an electrical schematic diagram of the assembly of FIG. 25.
Figure 27:
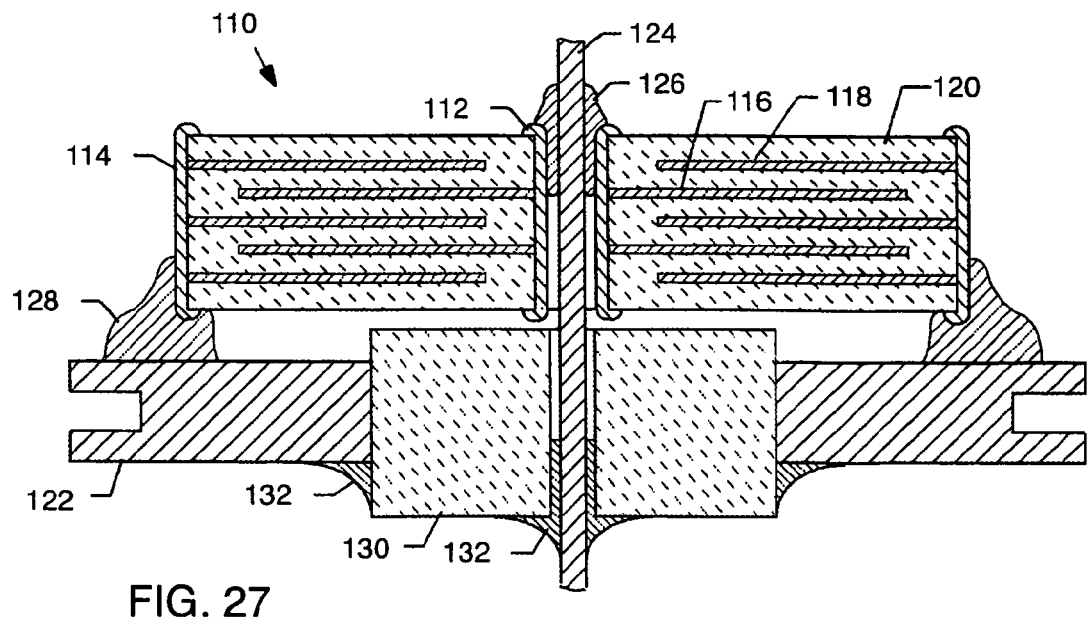
FIG. 27 is a cross-sectional view taken generally along line 27—27 of FIG. 25, illustrating internal components thereof and the use of non-migratable materials.

With reference now to FIGS. 25–27, the unipolar capacitor 110 is installed to a hermetic terminal 122, such as a ferrule, of a human implantable electronic device. As is well-known in the art, a lead wire or terminal pin 124 extends through the capacitor 110, the purpose of the capacitor 110 being to prevent EMI from disturbing or interrupting the function of internal circuitry and components of the implantable medical device. The hermetic terminal, or ferrule, is typically comprised of titanium or the like. While not of a noble metal or alloy thereof, titanium is biocompatible and is not migratable. The lead wire 124 should be coated with or solidly formed of a non-migratable material, typically gold or platinum or its alloys.

The electrical connecting material 126 between the lead wire 124 and the inner termination surface 112 must also be made of material that cannot migrate or form dendrites. Similarly, the electrical connection 128 between the outer termination surface 114 and the ferrule 122 must also be comprised of a bio-stable, non-migratable material. Such electrical connections 126 and 128 are typically comprised of thermal-setting conductive adhesives, welding or soldering materials. In a preferred embodiment, such thermal-setting conductive epoxies or polyimides would comprise gold or other biocompatible metals as a conductive filler. Said fillers may be in powder form. Other suitable filler materials include platinum, or platinum coated spheres of niobium or tantalum. As the capacitor's outer surface metallization is typically of pure gold or pure gold plating, the connection between the pure gold and the titanium is typically done with a gold-filled conductive polyimide. In a similar manner, the connection between the lead wire 124 which may be comprised of platinum iridium and the capacitor's inside diameter 112 which is typically comprised of gold, is preferably a gold-filled conductive polyimide. Alternative materials, such as gold brazing compound or the like, which forms a non-migratable material, may also be used. Such gold brazed material is pure gold, pure platinum, or equivalent such that it is noble and therefore does not migrate. A special platinum or gold bearing fired on glass frit may also be used. See Table 1 above.

With respect to the conductive connections, a conductive polyimide is preferable to a conductive epoxy because of its generally higher temperature rating, although either may be used. An alternative to the use of a conductive thermal-setting adhesive would be the use of a non-migratable weld, braze or solder compound, such as pure gold braze or weld.

With particular reference to FIG. 27, an insulator 130 is disposed between the ferrule 122 and the lead wire 124. The interface between the insulator 130 and the terminal pin 124 and ferrule 122 must be hermetically sealed. Such seal 132 is comprised of a suitable biocompatible material such as pure gold braze or TiCuSil or CuSil. It should be noted that TiCuSil and CuSil are brazing alloys that bind up the silver so tightly that it cannot readily migrate and form a dendrite.

Thus, the capacitor 110 and assembly illustrated in FIGS. 21–27 is comprised of materials that have been constructed of suitable non-migratable materials, such as noble metals, such that even in the presence of body fluid and bias voltage would not migrate and form a dendrite. That is, the capacitor inside and outside termination surface diameters 112 and 114, the active and ground electrodes 116 and 118, the lead wire 124, and connective materials 126, 128 and 132 are all non-migratable material, at least where exposed to the body fluid. Thus, dendritic growth is prevented.

Figure 28:
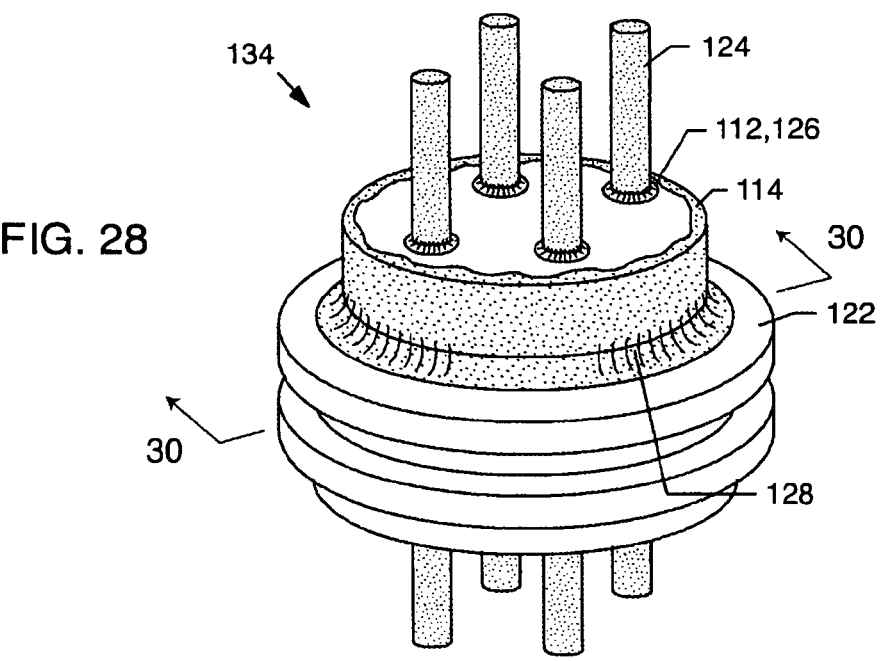
FIG. 28 is an isometric view of a quadpolar surface mounted capacitor in accordance with the present invention.
Figure 29:
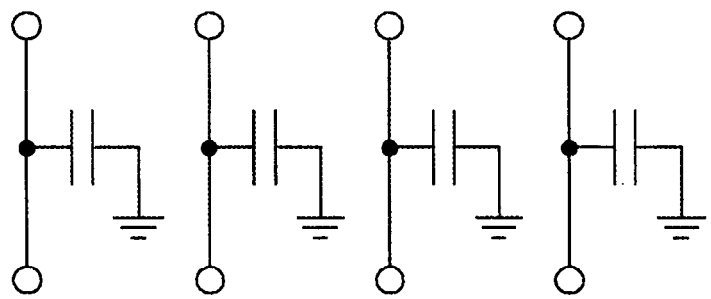
FIG. 29 is an electrical schematic diagram of the capacitors of FIG. 28.
Figure 30:
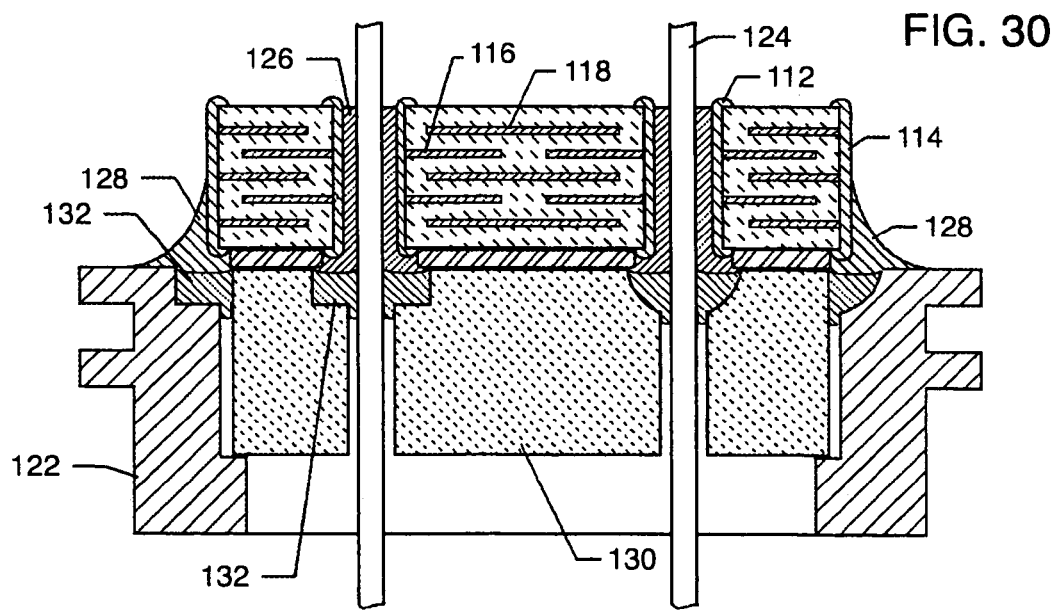
FIG. 30 is a cross-sectional view taken generally along line 30—30 of FIG. 28, illustrating internal components thereof and the use of non-migratable materials.

With reference now to FIGS. 28–30, the present invention is not limited in the type or configuration of capacitor used. A quadpolar surface mounted feedthrough capacitor 134 is illustrated in these figures and, as discussed above, is entirely constructed of non-migratable materials, at least where exposed to body fluids and moisture. Thus, all of the materials exposed to the body fluid side are made of materials that will not form dendrites or migrate. That is, the portion of the lead wire 124, inner surface metallization 112, connective material 126, outer termination surface 114, and connective material 128 to the ferrule 122 which are exposed to the body fluid are comprised of such non-migratable materials as described above. Preferably, the electrodes 116 and 118 as well as the seals 132 of the insulator 130 are also comprised of non-migratable materials as described above.

As mentioned above, the lead wires 124 and inner and outer metallization 112 and 114 of the capacitor can be plated, such as depositing electroplated nickel first then overplating with pure gold or the like plating, or otherwise coated with the non-migratable material. Alternatively, they are comprised of such materials.

Figure 31:
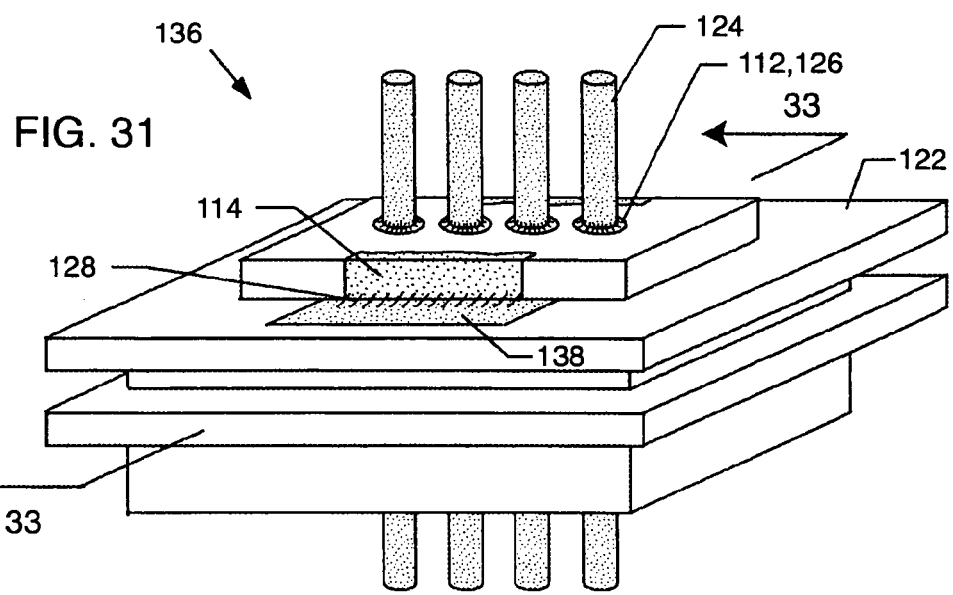
FIG. 31 is an isometric view of an inline quadpolar capacitor assembly embodying the present invention and incorporating non-migratable materials.
Figure 32:
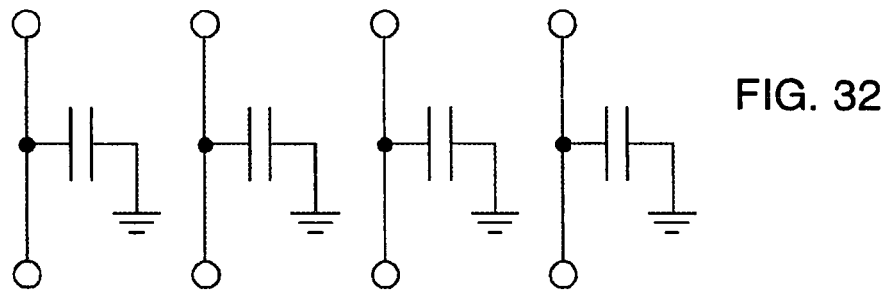
FIG. 32 is an electrical schematic diagram of the capacitor assembly of FIG. 31.
Figure 33:
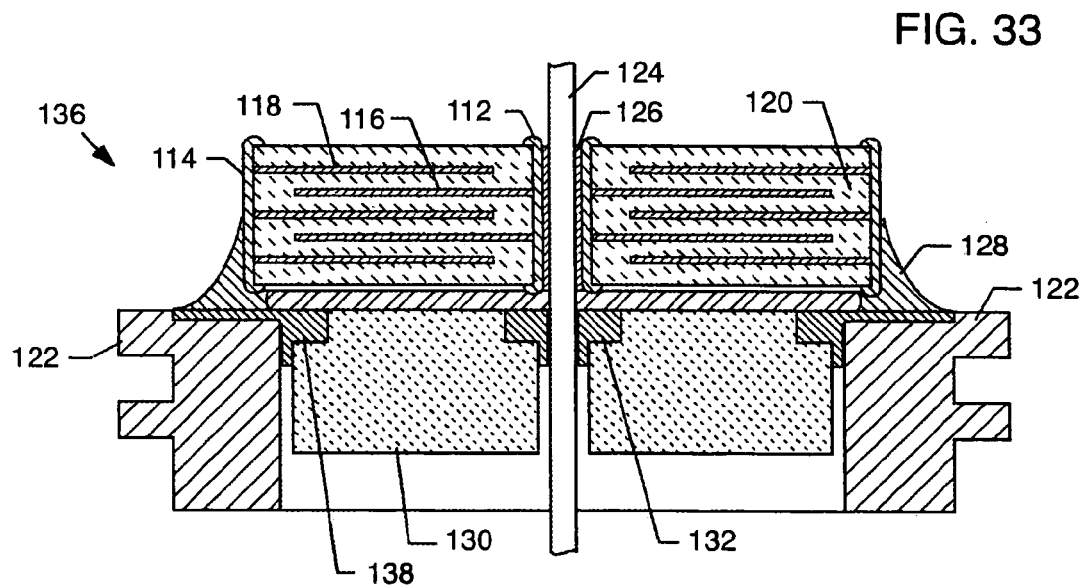
FIG. 33 is a cross-sectional view taken generally along line 33—33 of FIG. 31, illustrating internal components thereof.

With reference now to FIGS. 31–33, an in-line quadpolar capacitor 136 is shown surface mounted on the body fluid side of the hermetic terminal 122 of a human implantable medical device. The lead wires or terminal pins 124 are coated with or formed of a non-migratable material, such as a noble metal including gold or platinum. Similarly, as described above, the connection 126 between the inner termination surface 112 and the lead 124 is a non-migratable material, such as those described in Table 1 above. In this embodiment, a novel hermetic terminal with gold bond pads 138 is used. A non-migratable conductive connector 128, such as gold or platinum filled thermal-setting conductive polyimide or pure gold braze or the like is used to connect the outer termination surface 114 to the gold bond pad 138. Thus, on the body fluid side, those portions of conductive components which are exposed to the body fluid are comprised of non-migratable materials to prevent the formation of dendrites.

Figure 34:
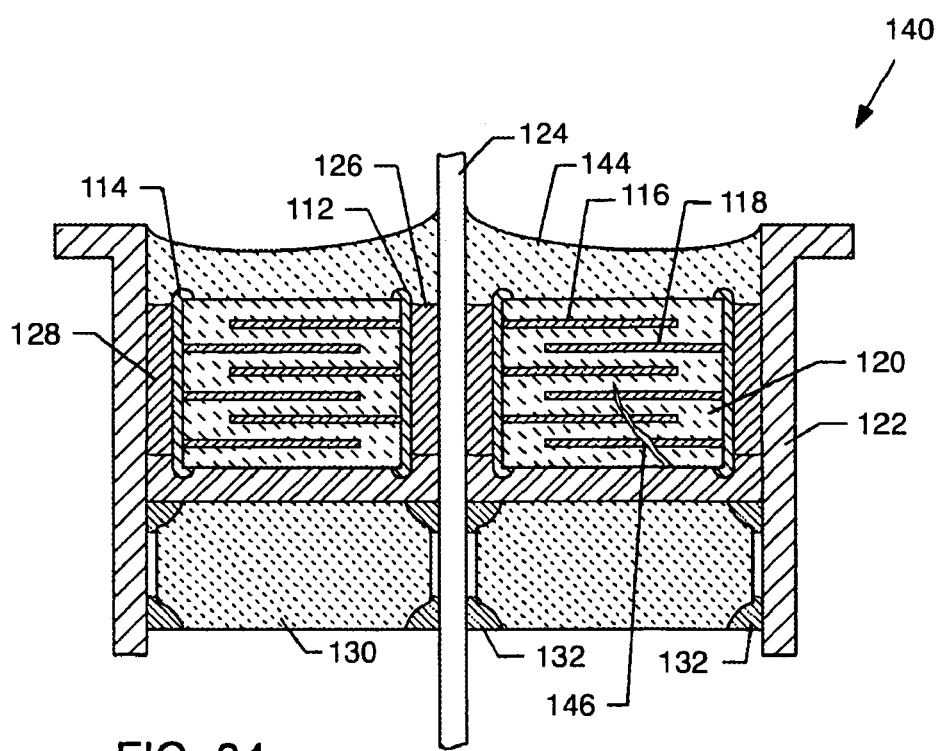
FIG. 34 is a cross-sectional view similar to FIG. 1, but illustrating use of non-migratable materials in accordance with the present invention and thus having a crack between electrodes thereof without dendritic growth.
Figure 35:
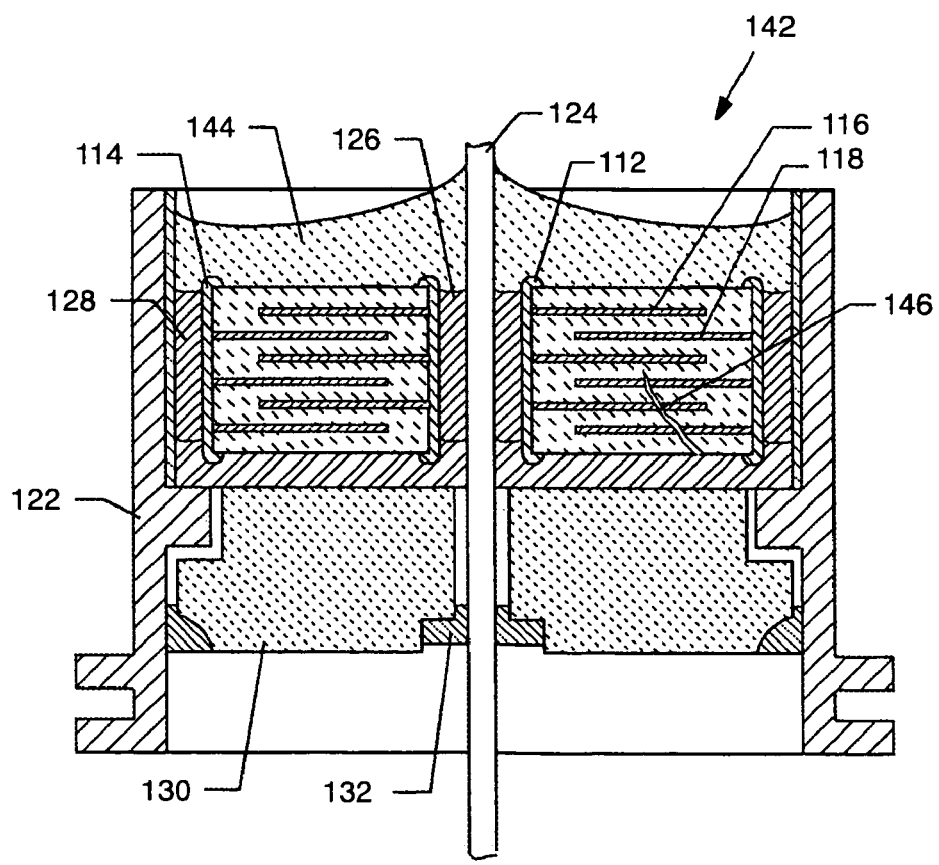
FIG. 35 is a cross-sectional view of another feedthrough capacitor having a crack therein and without dendritic growth due to the use of non-migratable materials in accordance with the present invention.

With reference to FIGS. 34 and 35, capacitor assemblies 140 and 142 are illustrated comprised of the non-migratable materials as discussed above, and having a sealant 144, such as the epoxy sealant disclosed in U.S. Pat. No. 6,055,455, the contents of which are incorporated by reference herein. In this case, the capacitors 140 and 142 are deliberately shown with fractures or cracks 146, resulting during the manufacturing process as described above. However, it will be noted that these cracks have no metal migration or dendrite within them. This is due to the fact that the capacitors 140 and 142 are entirely constructed of materials that do not migrate. This includes the lead wire terminal pin 124, inner and outer termination surfaces 112 and 114, electrodes 116 and 118, and connective materials 126 and 128. Thus, even a fairly large crack in the capacitor 140 or 142 does not present a long-term reliability problem, particularly for a low-voltage device. This is due to the fact that no harmful metal migration in the form of dendrites is possible.

Accordingly, in both capacitor structures 140 and 142, the penetration through the non-conductive sealing epoxy 144, shown on the top of the capacitor, is not a problem. Even though it is expected that over a long period of time body fluid would penetrate through the covering epoxy 144 through bulk permeability or through micro-separations due to lack of adhesions, the capacitor and its interconnections have been all constructed in accordance with the present invention so as not to be comprised of migratable materials, thus preventing the formation of insulation resistance reducing dendrites.

FIGS. 36–42 show an internally grounded bipolar capacitor 148 embodying the present invention. The capacitor 148 is designed to be surface mounted to a hermetic terminal 122, such as the illustrated ferrule. Capacitor 148 has been specially prepared during manufacturing to lay down a very thin layer of glass 150 on at least its top surface, and preferably both its top and bottom surfaces, as illustrated. It has been found that such glass layers 150 not only render the overall capacitor 148 stronger that it will better resist both mechanical and thermal stress during handling, installation and assembly of the implantable medical device, but also optimizes the capacitors 148 resistance to moisture or penetration by fluids. Thus, unlike the aforementioned epoxy sealants, the use of a glass sealant may provide sufficient resistance to penetration by fluids so as to enable a capacitor of migratable materials to be placed on the body fluid side. However, in a particularly preferred embodiment, the conductive components which might be exposed to the body fluid are comprised of non-migratable material to ensure that the harmful metal migration and dendrite formation discussed above will not occur.

Applying the glass layer 150 can be done in various manners. For example, after capacitor firing, the capacitor can be run through a glass-sealing kiln very near the melting point of the glass, but just below it. The capacitor 148 would be placed on glass sheets which would be run through the furnace allowing some of the glass to diffuse into the surfaces of the ceramic capacitor 148. The glass has the effect of reducing some of the capacitor porosity and filling it with insulating glass. This cuts down on any tendency to form a dendrite and also makes the capacitor itself more moisture resistant. Another technique of applying the glass layer 150 would be the use of a fine glass or ground powdered glass, or a paste like frit which would be applied to the capacitor which is then run through a firing furnace. High volume applications could be by silk-screening or spray processes After the manufacturing of the ceramic capacitor 148 at very high temperature, it would be possible to lay down a very thin glass layer, which would be fired or co-fired into place.

Figure 36:
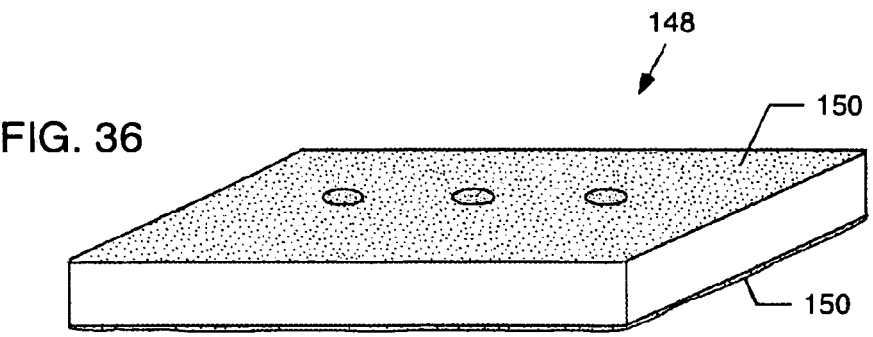
FIG. 36 is a perspective view of an internally grounded biopolar capacitor layered with glass in accordance with the present invention.
Figure 37:
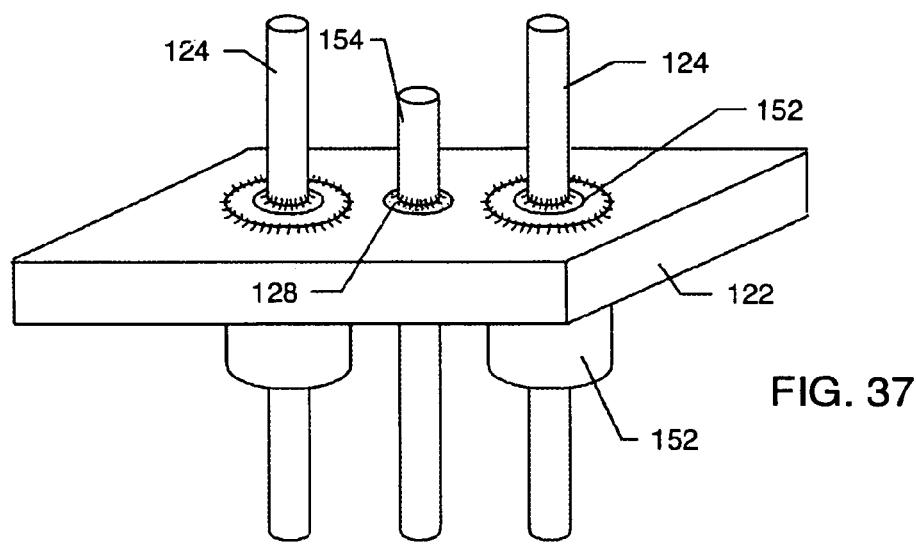
FIG. 37 is a perspective view of a hermetic terminal, having terminal pins or lead wires extending therethrough.

The capacitor 148 of FIG. 36 is designed to be mounted to a hermetic terminal, such as the ferrule 122 illustrated in FIG. 37. This ferrule has been simplified into a rectangular shape, although in actual practice it can take have many flanges and take on many shapes and configurations depending upon its application. The two outer most leads 124 are formed in insulative relationship with conductive ferrule 122 by use of insulating connectors or sealants 152. The center lead wire, or ground wire 154 is grounded and directly brazed or welded to the conductive ferrule 122 using non-migratable material 128, such a gold braze or the like. The grounded pin 154, which is brazed or welded to the ferrule 122 with a non-migratable material 128 is the connection point for the capacitor's internal ground electrode plates 118.

Figure 39:
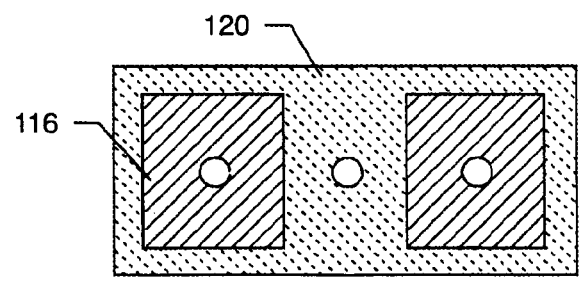
FIG. 39 is a cross-sectional view illustrating the configuration of active electrode plates in the capacitor of FIG. 36.
Figure 40:
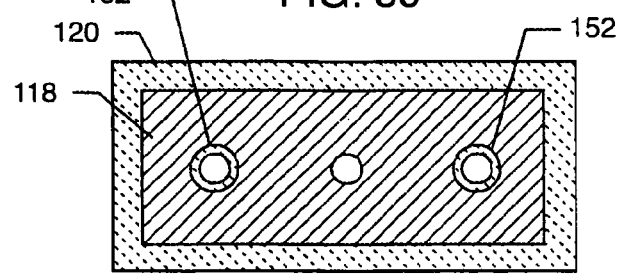
FIG. 40 is a cross-sectional view illustrating the configuration of ground electrode plates in the capacitor of FIG. 36.
Figure 38:
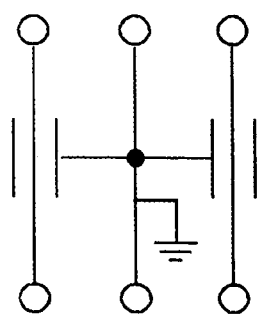
FIG. 38 is an electrical schematic diagram of the capacitor of FIG. 36.
Figure 41:
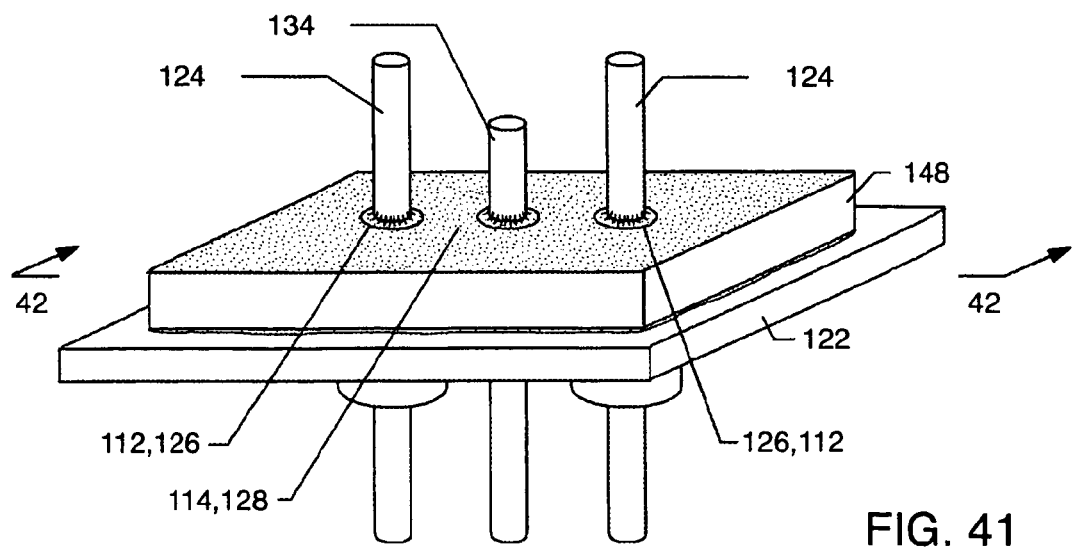
FIG. 41 is a perspective view of the capacitor of FIG. 36 attached to the hermetic terminal of FIG. 37.
Figure 42:
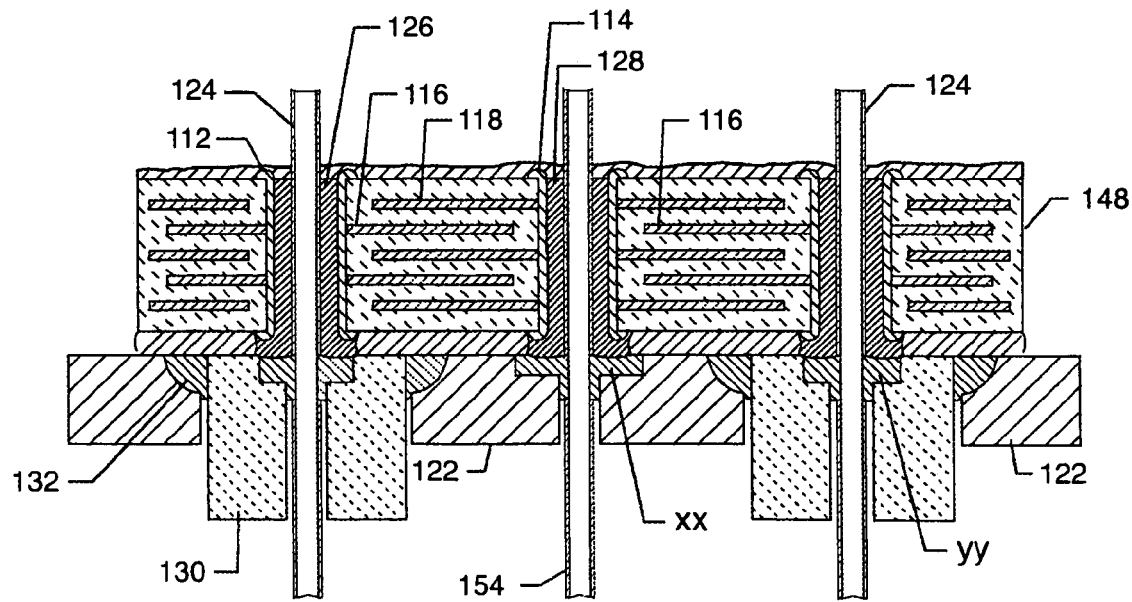
FIG. 42 is a cross-sectional view taken generally along line 42—42 of FIG. 41, illustrating internal components of the assembly, and a glass layer thereon.

FIGS. 39 and 40 illustrate the active and ground electrode plates used in such a configuration, such as that described in U.S. Pat. No. 5,905,627. With reference now to FIGS. 41 and 42, as discussed above, preferably the capacitor 148 and assembly are manufactured in accordance with the teachings of the present invention. That is, the internal electrode plates 116 and 118 are comprised of platinum or alloys of gold, platinum or palladium. Other electrode compositions that would not migrate in the presence of body fluids are also acceptable. Moreover, the conductive connections 126 and 128 are comprised of non-migratable thermosetting or brazing material such as that described above. The hermetic seal mechanical connections 132 are preferably comprised of a gold braze of the like. An alternative to this would be to use a glass seal where a compression or a fusion seal is formed between the ferrule and the outer lead wires 124 such that no metal joining is required at all.

One advantage of the internally grounded capacitor 148 is that it does not require any perimeter or outer termination metallization at all. Neither does it require any electrical or mechanical connection between the capacitor 148 and the metallic ferrule 122 as this connection occurs between the ground terminal pin 154 and the ferrule 122. As there is no capacitor outer metallization, the connectors 128 between the ground lead wire 154 and the ferrule 122 are comprised of non-migratable materials, as are the seals and connectors 132 between the insulators 130 and the ferrule 122. Of course, the connective material 126 between in the inner diameter termination surfaces 112 and the lead wires 124 are comprised of non-migratable materials as well.

Figure 43:
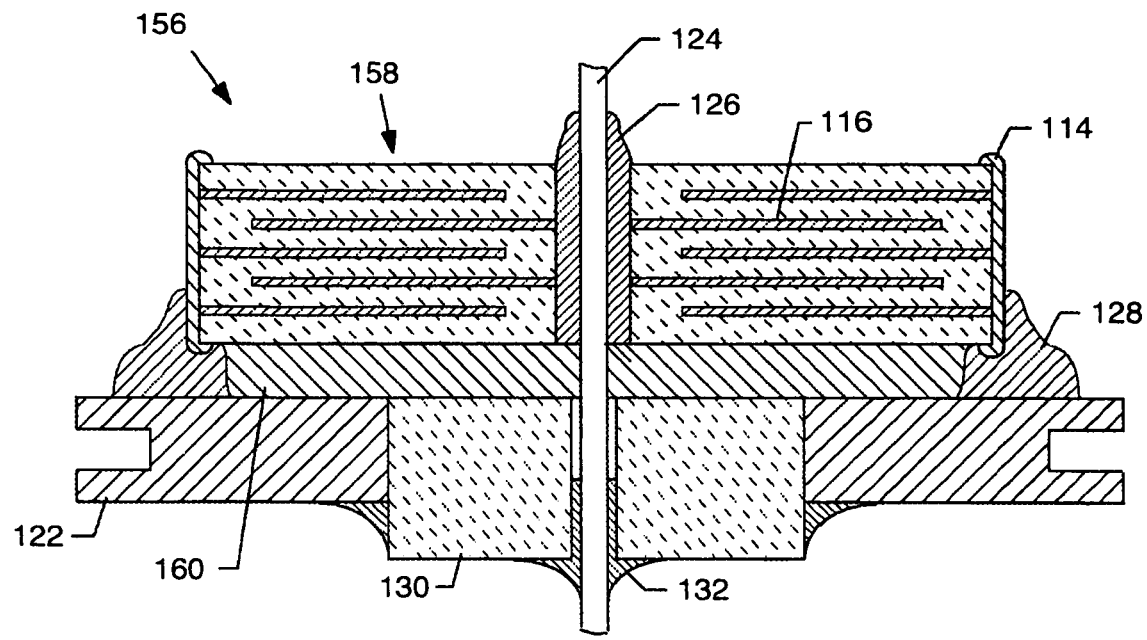
FIG. 43 is a cross-sectional view of a feedthrough capacitor assembly, wherein the inner metallization of the capacitor has been removed in accordance with the present invention.

With reference now to FIG. 43, all prior art monolithic ceramic capacitors have been constructed with termination materials. Such termination materials cover both rectangular MLC chip capacitors and feedthrough chip capacitors with one or more passageways. The reasons for such termination metallization materials are: (1) to provide electrical connection to the active and ground electrode plates, which are set in parallel; and (2) to provide a surface wherein one can solder or otherwise make conductive attachments from the capacitor to other components in the circuitry. In the specific case of a human implant device as illustrated and described above, termination metallization materials are utilized in the connection from the capacitor active electrode plates and terminal pin or lead wire, and the connection between the capacitor ground electrode plates and the metallic ferrule.

The assembly 156 illustrated in FIG. 43 is similar to that illustrated and described above in FIGS. 25–27, except that the feedthrough capacitor 158 does not include an inner termination metallization surface, shown by the reference number 112 in FIGS. 25–27. Instead, the lead wire or terminal pin 124 is conductively coupled to the set of active electrodes 116 of the capacitor 158 solely with the electrical connective material 126. As discussed above, the connective material 126 is non-migratable and can be comprised of such materials as gold or platinum-filled thermal-setting conductive polyimide or any other conductive material that has been loaded with suitable particles such as gold or platinum such that it can make a direct electrical contact with the one or more electrodes 124 and be biocompatible.

It is important that the conductive thermal-setting material 126 penetrate all the way down through the one or more passageways of the feedthrough capacitor 158. This is best accomplished by injection or centrifuging. Accordingly, it is important that this material 126 not be allowed to extend underneath the capacitor 158 such that it could cause a short between the ferrule 122 or the outer metallization 114, which is still present in the embodiment illustrated in FIG. 43. Accordingly, an insulating material or insulating washer 160 is disposed below the capacitor 158 to prevent material 126 from migrating or penetrating into areas where it would be undesirable. In a particularly preferred embodiment, the insulating material 160 is an adhesively coated polyimide washer.

Of course, as discussed above, the one or more electrodes 124 would also be of non-migratable material such as a noble metal including platinum or gold or an alternative alloy consisting of gold platinum and palladium. The thermal-setting conductive material 128 used to electrically connect the conductive ferrule 122 with the outer metallization 114 of the capacitor 158 is comprised of non-migratable materials as described above.

Whereas the present invention is primarily directed to human implanted devices and applications, the embodiments illustrated in FIG. 43 have much broader application for all feedthrough capacitors whether they be for medical implant or not. The concept of making electrical connection from a lead wire or to the outside diameter without the need for termination material has obvious advantages to those skilled in the art. It is very labor-intensive to apply these termination materials, which involve several process and termination firing steps. Eliminating the inner termination surface 112 and electrically coupling the lead wire 124 directly to the active electrode plates 116 with material 126 eliminates a number of process steps relating to prior art capacitor inside diameter termination material.

Figure 44:
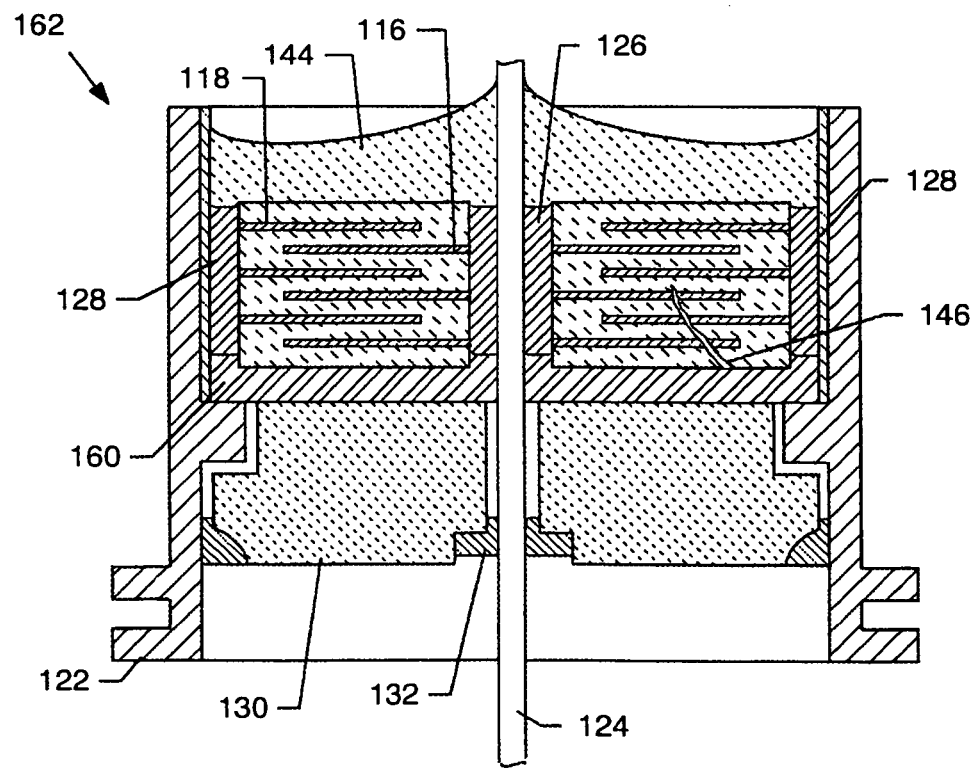
FIG. 44 is a cross-sectional view of another feedthrough filter assembly, wherein the inner and outer metallization of the capacitor has been eliminated in accordance with the present invention.

With reference now to FIG. 44, a feedthrough capacitor assembly 162 is illustrated which is similar to that illustrated in FIG. 35. However, the feedthrough capacitor 164 embedded within the surrounding metallic ferrule 122 does not include inside diameter or outside diameter metallization (labeled with reference numbers 112 and 114 in FIG. 35). Instead, the one or more feedthrough holes, which may be of any geometry, are filled with the conductive material 126, as described above in relation to FIG. 43. Conductive material 128, which may comprise the same material as 126, directly conductively couples the second set of ground electrode plates 118 to the hermetic terminal ferrule 122. Once again, insulative material, typically in the form of a washer 160, prevents shorting of the capacitor.

Figure 45:
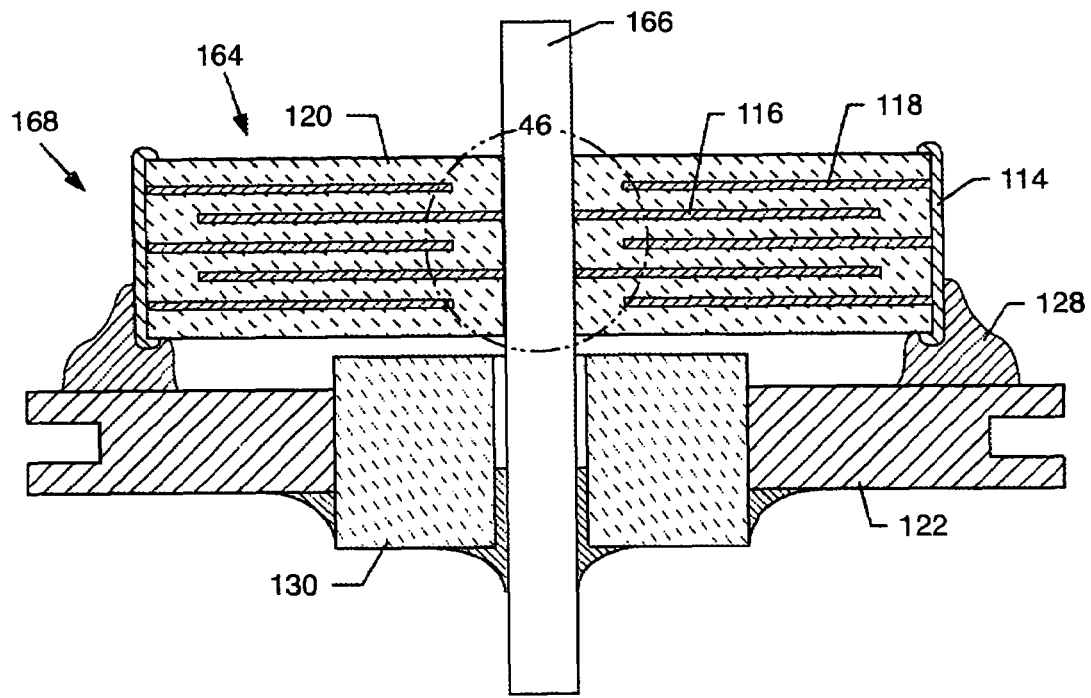
FIG. 45 is a cross-sectional view of a feedthrough filter capacitor assembly, wherein a terminal pin directly contacts the active electrode portions of the capacitor in accordance with the present invention.
Figure 46:
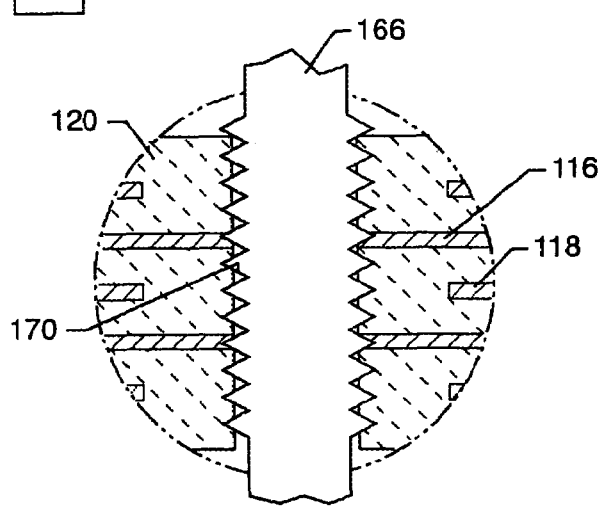
FIG. 46 is an enlarged sectional view taken generally from area "46" of FIG. 45, illustrating a knurled or roughened portion of the terminal pin.

With reference now to FIG. 45, yet another assembly 164 is illustrated which shows an alternative method of electrically coupling a terminal pin or electrical lead 166 to the internal electrode set 116 of the capacitor 168. In this case, the pin or wire 166 is designed to form a very tight or pressed fit within the inside diameter or passageway of the capacitor 168. In the instance of an inner metallization material 112, a mechanical connection is made between the lead wire 166 and the capacitor metallization 112. As illustrated in FIG. 45, the inner metallization 112 may be absent such that the active electrode plates 116 directly contact the terminal pin or electrical lead wire 166 either through the enlargement of the terminal pin 166 or the reduction in diameter of the passageway through the capacitor 168. In a particularly preferred embodiment, the electrical lead 166 has been prepared prior to inserting with a knurled, sputtered or roughened area 170 which coincides with the internal electrode set 116 to increase the electrical contact surface area to either the capacitor metallization 112 or directly to electrodes 116.

It will be appreciated by those skilled in the art that the embodiments illustrated in FIGS. 43–46 incorporate the non-migratable materials previously discussed so as to have application in implantable biomedical devices in which the components of the EMI filter assembly, including the capacitor, are exposed to body fluid. The selection and use of the non-migratable materials and the construction of the capacitor, terminal pin or lead wire, and conductive connections provide a biocompatible surface which prevents dendritic growth and the like.

Figure 47:
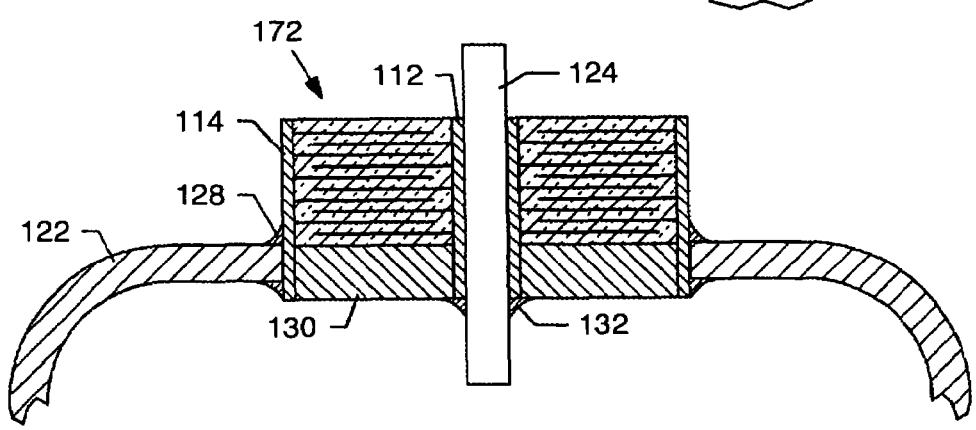
FIG. 47 is a cross-sectional view of an integrated feedthrough capacitor assembly embodying the present invention.

With reference now to FIG. 47, an integrated feedthrough capacitor 172 is illustrated, as previously described in U.S. Pat. No. 6,008,980, the contents of which are incorporated herein. A novel feature of this patent is that the feedthrough capacitor 172 itself becomes its own hermetic seal. This is desirable as it eliminates a number of components and process steps. Incorporating the use of non-migratable materials in accordance with the present invention and as described above allows the capacitor 172 to be placed on the body fluid side of the hermetic seal.

In the previously illustrated and described embodiments, the capacitors have been feedthrough capacitors. However, it will be appreciated by those skilled in the art that the present invention is not limited to such feedthrough capacitors.

Figure 48:
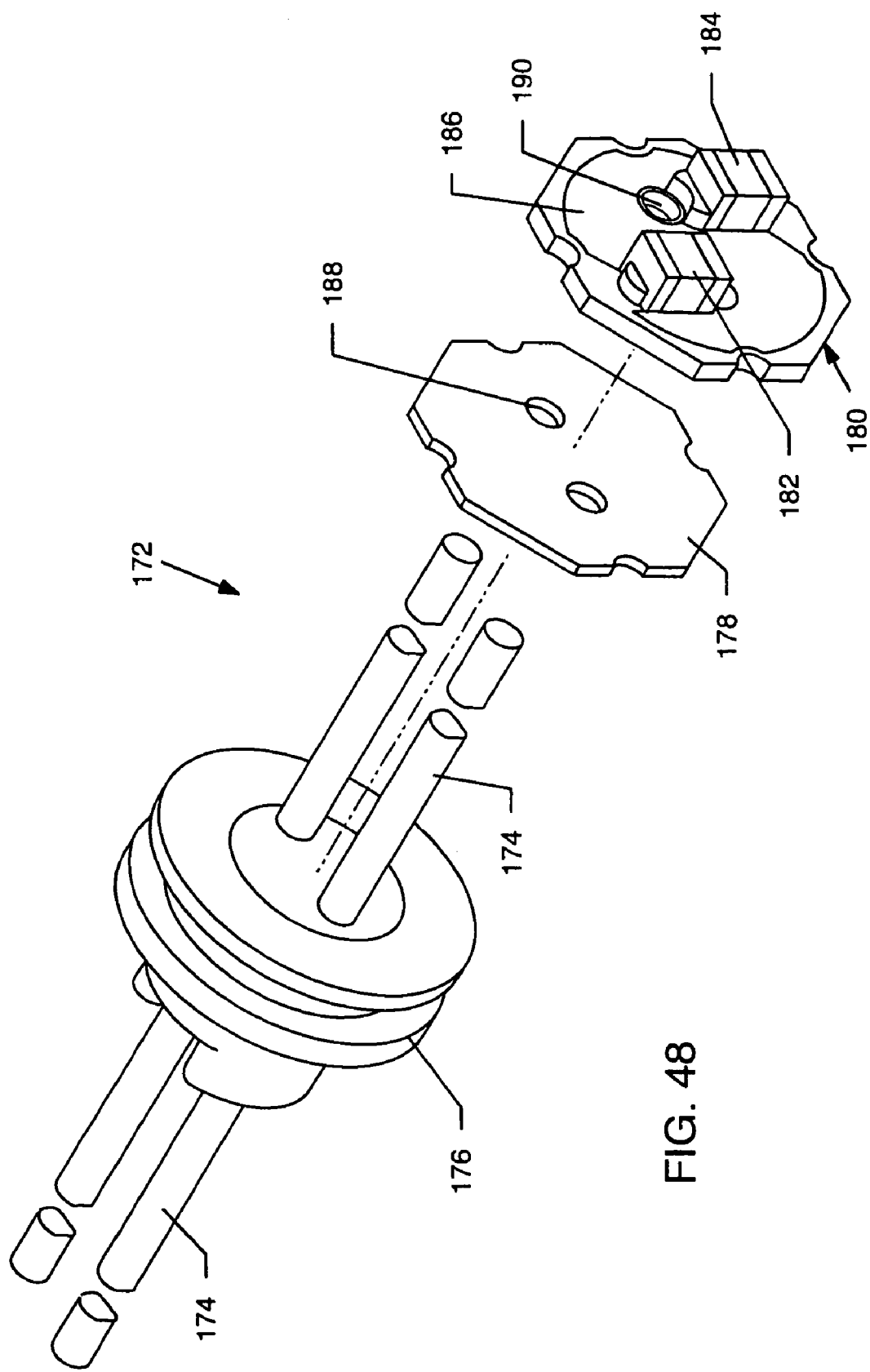
FIG. 48 is a partially fragmented exploded perspective view of a multi-lead feedthrough showing an insulating sheet between the feedthrough and filter support assembly and incorporating chip capacitors in accordance with the present invention.

With reference now to FIG. 48, an EMI filter assembly 172 is shown which is similar to that illustrated and described in U.S. Pat. No. 5,896,267, the contents of which are incorporated by reference herein. The assembly 172 includes multiple leads 174 extending through feedthrough 176 and insulating film 178. A capacitor support assembly 180 supports two chip capacitors 182 and 184. Insulating film 178 is disposed between the multi-lead feedthrough 176 in the capacitor support assembly 180. Of course, the arrangement is applicable to feedthrough assemblies of any number of leads. Insulating film 178 is shaped to contour match that of the substrate 186. The leads 174 extend through lined apertures 188 and 190 of the insulating film 178 and substrate 186. As such, the leads 174 do not extend through the chip capacitors 182 and 184, but the chip capacitors 182 and 184 are designed so as to present active and ground electrode surfaces which interact with the leads 174 and grounding terminal, as described in U.S. Pat. No. 5,896,267. The capacitors 182 and 184 and the pertinent conductive connection materials, leads 174, etc. are coated or comprised of non-migratable materials as discussed above so as to be placed on the body fluid side of the applicable implantable device outside of the hermetic terminal.

Thus, it will be appreciated by those skilled in the art that manufacturing feedthrough filter capacitor assemblies in accordance with the teachings of the present invention, namely, the use of non-migratable material such as noble metals and the like, and/or glass sealing layers, allows the capacitor to be disposed outside of the housing of the medical device without the formation of harmful dendrites due to metal migration. The free space within the housing can enable the housing to be smaller, incorporate a larger battery, more sophisticated electronics. Other benefits will be appreciated by those skilled in the art.

Although several embodiments of the present invention have been described in detail for purposes of illustration, various modifications of each may be made without departing from the spirit and scope of the invention. Accordingly, the invention is not to be limited, except as by the appended claims.

What is claimed is:

1. An EMI filter capacitor assembly for an active implantable medical device, comprising:
   a capacitor directly exposed to body fluid when implanted, including first and second sets of electrode plates comprising a non-migratable and biocompatible material;
   a conductive hermetic terminal comprising a non-migratable and biocompatible material adjacent to the capacitor and in conductive relation to the second set of electrode plates; and
   a conductive terminal pin having an outer surface comprising a non-migratable and biocompatible material at least where exposed to body fluid in conductive relation with the first set of electrode plates, the terminal pin extending through the hermetic terminal in non-conductive relation.

2. The assembly of claim 1, wherein the first and second sets of electrode plates comprise a noble metal or noble metal composition.

3. The assembly of claim 2, wherein the first and second sets of electrode plates comprise gold, platinum, a gold-based alloy, or a platinum-based alloy.

4. The assembly of claim 1, wherein the outer surface of the terminal pin comprises a noble metal or a noble metal composition.

5. The assembly of claim 4, wherein the outer surface of the terminal pin comprises gold, platinum, titanium, niobium, tantalum, a gold-based alloy, or a platinum-based alloy.

6. The assembly of claim 1, wherein the outer surface of the terminal pin directly contacts the first set of electrode plates.

7. The assembly of claim 1, wherein the capacitor includes a first termination surface comprising a non-migratable and biocompatible material conductively coupled to the first set of electrode plates and the terminal pin.

8. The assembly of claim 7, wherein the first termination surface comprises a noble metal or a noble metal composition.

9. The assembly of claim 8, wherein the first termination surface comprises gold, platinum, a gold-based alloy, or a platinum-based alloy.

10. The assembly of claim 7, wherein the terminal pin directly contacts with the first termination surface.

11. The assembly of claim 7, including a connection material comprising a non-migratable and biocompatible material conductively coupling the terminal pin and the first termination surface.

12. The assembly of claim 11, wherein the connection material comprises a brazing, welding or soldering material.

13. The assembly of claim 12, wherein the brazing, welding or soldering material is selected from the group consisting of: titanium, platinum and platinum/iridium alloys, tantalum, niobium, zirconium, hafnium, nitinol, Co—Cr—Ni alloys, stainless steel, gold, ZrC, ZrN, TiN, NbO, TiC, TaC, gold-bearing glass frit, TiCuSil, CuSil, and gold-based braze.

14. The assembly of claim 11, wherein the connection material comprises a conductive thermal-setting material.

15. The assembly of claim 14, wherein the thermal-setting material comprises a polymer selected from the group consisting of: epoxies, polyimides, polyethylene oxide, polyurethane, silicone, polyesters, polycarbonate, polyethylene, polyvinyl chloride, polypropylene, methylacrylate, para-xylylene, and polypyrrhol.

16. The assembly of claim 15, wherein the thermal-setting material includes a non-migratable and biocompatible conductive filler.

17. The assembly of claim 16, wherein the conductive filler is selected from the group consisting of titanium, platinum and platinum/iridium alloys, tantalum, niobium, zirconium, hafnium, nitinol, Co—Cr—Ni alloys, stainless steel, gold, ZrC, ZrN, TiN, NbO, TiC, TaC.

18. The assembly of claim 1, wherein the second set of electrode plates directly contacts the hermetic terminal.

19. The assembly of claim 1, including a connection material comprising a non-migratable and biocompatible material conductively coupling the second set of electrode plates and the hermetic terminal.

20. The assembly of claim 1, wherein the capacitor includes a second termination surface comprising a non-migratable and biocompatible material conductively coupled to the second set of electrode plates and the hermetic terminal.

21. The assembly of claim 20, wherein the second termination surface comprises a noble metal or a noble metal composition.

22. The assembly of claim 21, wherein the second termination surface comprises gold, platinum, a gold-based alloy, or a platinum-based alloy.

23. The assembly of claim 20, including a connection material comprising a non-migratable and biocompatible material conductively coupling the second termination surface and the hermetic terminal.

24. The assembly of claim 23, wherein the connection material comprises a brazing, welding or soldering material.

25. The assembly of claim 24, wherein the brazing, welding or soldering material is selected from the group consisting of: titanium, platinum and platinum/iridium alloys, tantalum, niobium, zirconium, hafnium, nitinol, Co—Cr—Ni alloys, stainless steel, gold, ZrC, ZrN, TiN, NbO, TiC, TaC, gold-bearing glass frit, TiCuSil, CuSil, and gold-based braze.

26. The assembly of claim 23, wherein the connection material comprises a conductive thermal-setting material.

27. The assembly of claim 26, wherein the thermal-setting material comprises a polymer selected from the group consisting of: epoxies, polyimides, polyethylene oxide, polyurethane, silicone, polyesters, polycarbonate, polyethylene, polyvinyl chloride, polypropylene, methylacrylate, para-xylylene, and polypyrrhol.

28. The assembly of claim 27, wherein the thermal-setting material includes a non-migratable and biocompatible conductive filler.

29. The assembly of claim 28, wherein the conductive filler is selected from the group consisting of titanium, platinum and platinum/iridium alloys, tantalum, niobium, zirconium, hafnium, nitinol, Co—Cr—Ni alloys, stainless steel, gold, ZrC, ZrN, TiN, NbO, TiC, TaC.

30. The assembly of claim 1, wherein the hermetic terminal comprises a material selected from titanium, platinum and platinum/iridium alloys, tantalum, niobium, zirconium, hafnium, nitinol, Co—Cr—Ni alloys, stainless steel, gold, ZrC, ZrN, TiN, NbO, TiC, and TaC.

31. The assembly of claim 1, including a biocompatible hermetic insulator disposed between the hermetic terminal and the terminal pin, and seal joints connecting the insulator and the hermetic terminal, the seal joints comprising a non-migratable and biocompatible material.

32. The assembly of claim 31, wherein the seal joints are selected from the group consisting of: titanium, platinum and platinum/iridium alloys, tantalum, niobium, zirconium, hafnium, nitinol, Co—Cr—Ni alloys, stainless steel, gold, ZrC, ZrN, TiN, NbO, TiC, TaC, gold-bearing glass frit, TiCuSil, CuSil, gold-based braze, and polymers including epoxies, polyimides, polyethylene oxide, polyurethane, silicone, polyesters, polycarbonate, polyethylene, polyvinyl chloride, polypropylene, methylacrylate, para-xylylene, and polypyrrhol.

33. The assembly of claim 1, including a glass layer covering a top surface of the capacitor.

34. The assembly of claim 33, including a glass layer further covering a bottom surface of the capacitor.

35. The assembly of claim 1, wherein the capacitor comprises a chip capacitor.

36. The assembly of claim 1, wherein the capacitor comprises a feedthrough capacitor having a passageway for permitting the terminal pin to extend therethrough.

37. The assembly of claim 36, wherein the capacitor includes multiple passageways for reception of multiple terminal pins therethrough, each terminal pin having an outer surface comprising a non-migratable and biocompatible material at least where exposed to body fluid.

38. The assembly of claim 1, wherein the active implantable medical device is selected from the group consisting of: cardiac pacemakers, cardioverter defibrillators, neurostimulators, internal drug pumps, cochlear implants, and ventricular assist devices.

* * * * *